United States Patent
Higuera et al.

(10) Patent No.: US 9,133,429 B2
(45) Date of Patent: Sep. 15, 2015

(54) HIGH THROUGHPUT MULTIWELL SYSTEM FOR CULTURING 3D TISSUE CONSTRUCTS IN-VITRO OR IN-VIVO, METHOD FOR PRODUCING SAID MULTIWELL SYSTEM AND METHODS FOR PREPARING 3D TISSUE CONSTRUCTS FROM CELLS USING SAID MULTIWELL SYSTEM

(75) Inventors: Gustavo Andres Higuera, Enschede (NL); Lorenzo Moroni, Enschede (NL); Clemens Antoni van Blitterswijk, Enschede (NL)

(73) Assignee: UNIVERSITEIT TWENTE, Enschede (NL)

( * ) Notice: Subject to any disclaimer, the term of this patent is extended or adjusted under 35 U.S.C. 154(b) by 158 days.

(21) Appl. No.: 13/808,399

(22) PCT Filed: Jul. 6, 2011

(86) PCT No.: PCT/NL2011/050486
§ 371 (c)(1),
(2), (4) Date: Mar. 18, 2013

(87) PCT Pub. No.: WO2012/005580
PCT Pub. Date: Jan. 12, 2012

(65) Prior Publication Data
US 2013/0174287 A1 Jul. 4, 2013

(30) Foreign Application Priority Data
Jul. 6, 2010 (EP) .................................... 10168610

(51) Int. Cl.
*C12N 5/00* (2006.01)
*C12M 1/12* (2006.01)
*C12M 1/18* (2006.01)
*B01L 3/00* (2006.01)
*C12M 3/00* (2006.01)
*C12M 1/32* (2006.01)
*C12M 1/00* (2006.01)

(52) U.S. Cl.
CPC ................ *C12M 1/18* (2013.01); *B01L 3/5085* (2013.01); *C12M 21/08* (2013.01); *C12M 23/12* (2013.01); *C12M 23/20* (2013.01); *B01L 2300/0829* (2013.01); *B01L 2300/163* (2013.01)

(58) Field of Classification Search
CPC ................ B01L 2300/0829; B01L 2300/0858; B01L 2300/163; B29C 66/71; B29C 45/16; C12M 23/12; C12M 21/08
See application file for complete search history.

(56) References Cited

U.S. PATENT DOCUMENTS

| | | | | |
|---|---|---|---|---|
| 6,719,449 B1 * | 4/2004 | Laugharn et al. | ............. | 366/127 |
| 2002/0172621 A1 * | 11/2002 | Barbera-Guillem | .......... | 422/100 |
| 2006/0019326 A1 * | 1/2006 | Vacanti et al. | ................... | 435/18 |
| 2007/0207537 A1 * | 9/2007 | Cui et al. | ................... | 435/288.4 |

FOREIGN PATENT DOCUMENTS

| | | | | |
|---|---|---|---|---|
| WO | WO 2010062911 A2 | * | 6/2010 | |
| WO | WO 2011025977 A2 | * | 3/2011 | |

* cited by examiner

*Primary Examiner* — Maria Leavitt
*Assistant Examiner* — Kimberly A Aron
(74) *Attorney, Agent, or Firm* — Lucas & Mercanti, LLP

(57) ABSTRACT

The invention relates to a multiwell system, characterized that said multiwell system having at least 3 wells, wherein said wells have a volume between 0.125 and 4.0 mm$^3$.

9 Claims, 18 Drawing Sheets

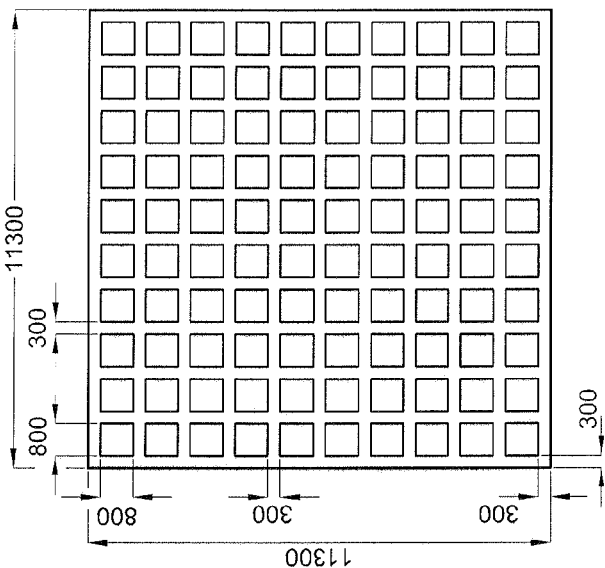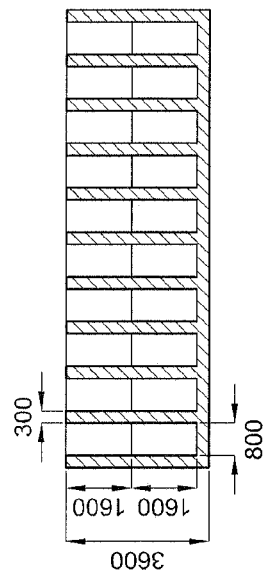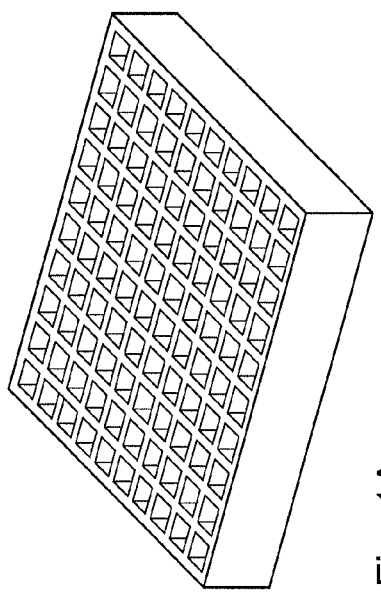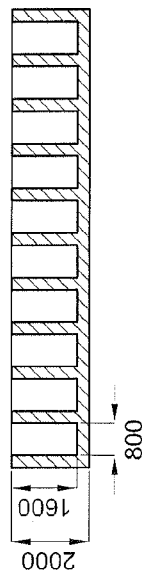

Figure 2:
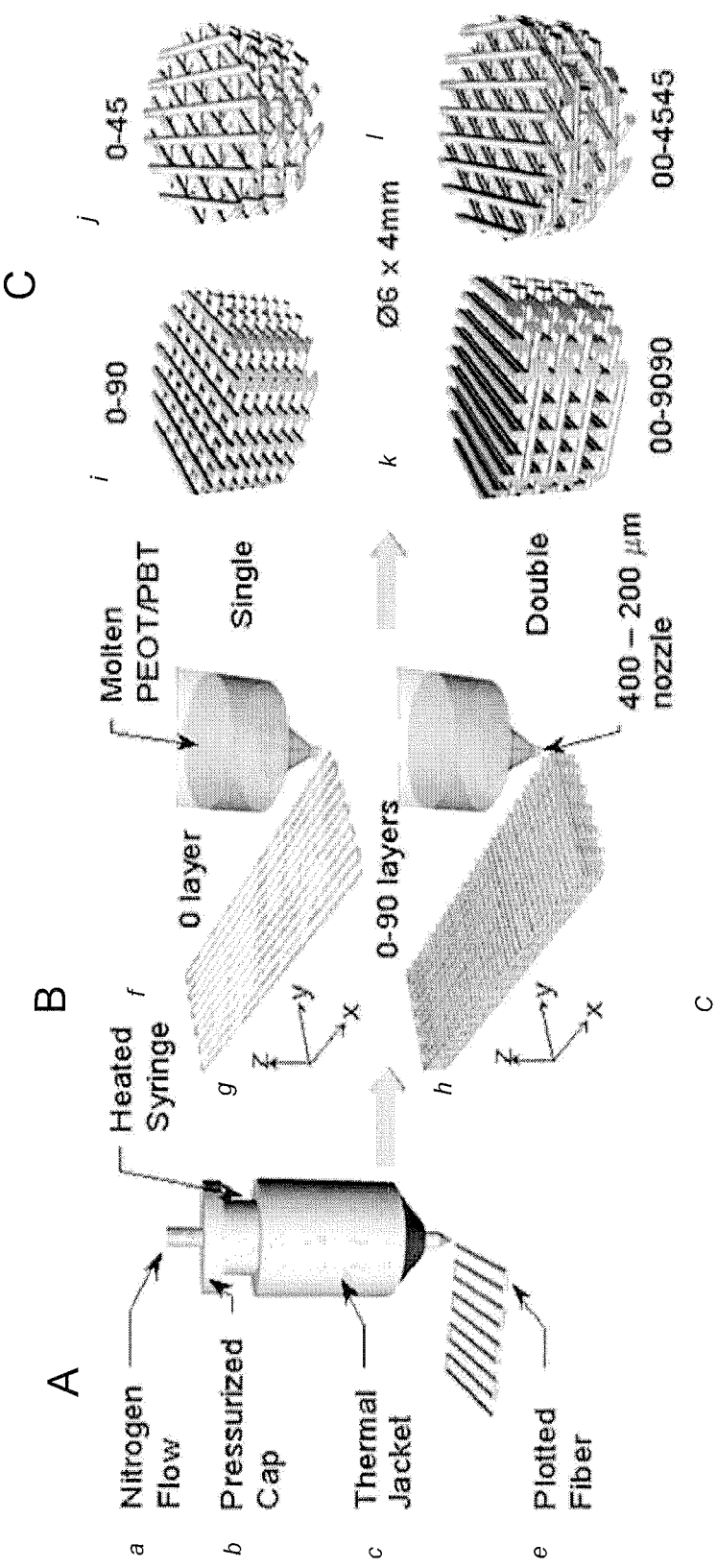

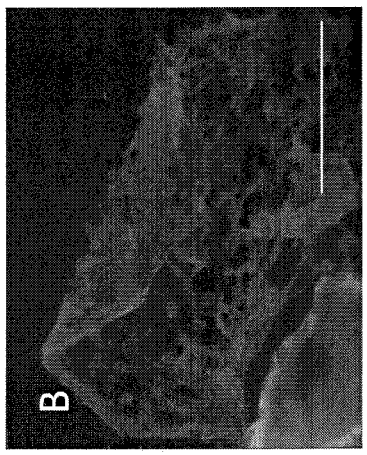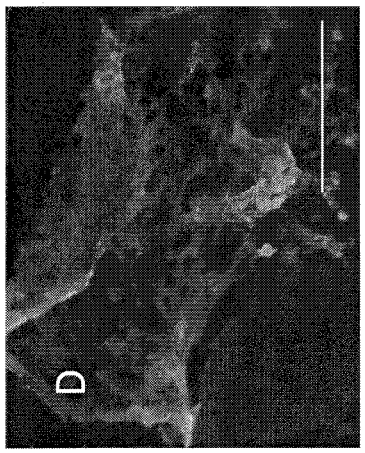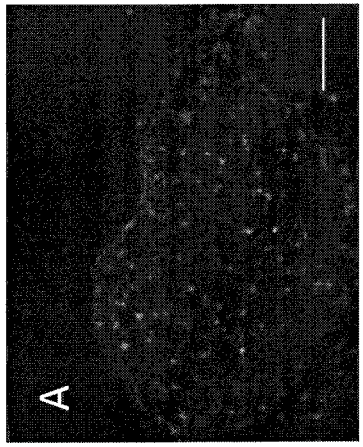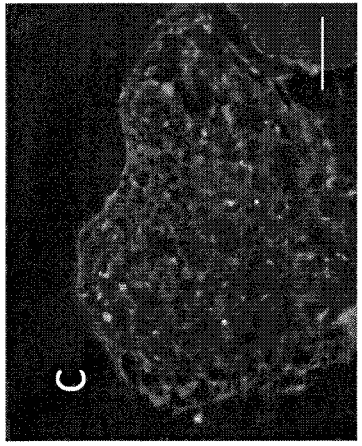
Figure 6

Figure 16
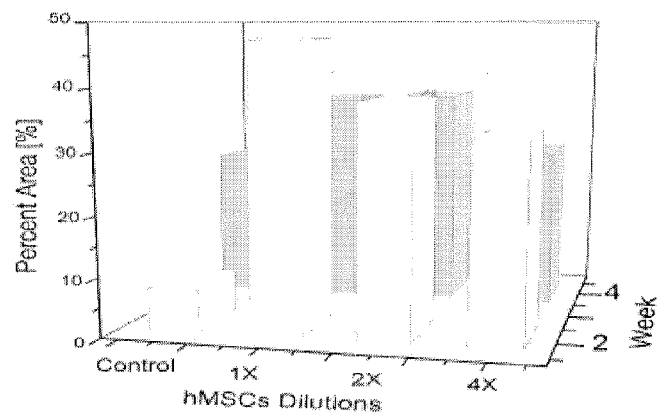
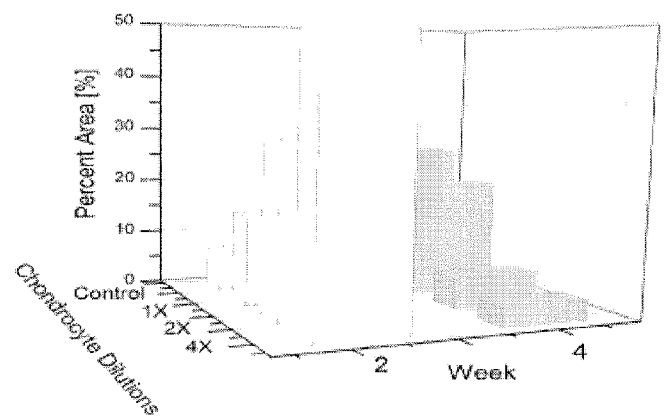
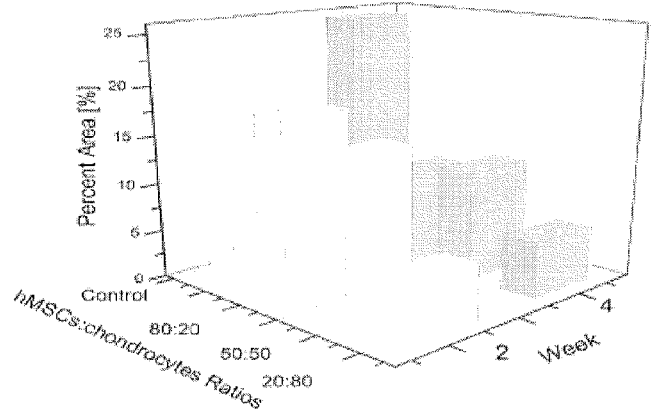

HIGH THROUGHPUT MULTIWELL SYSTEM FOR CULTURING 3D TISSUE CONSTRUCTS IN-VITRO OR IN-VIVO, METHOD FOR PRODUCING SAID MULTIWELL SYSTEM AND METHODS FOR PREPARING 3D TISSUE CONSTRUCTS FROM CELLS USING SAID MULTIWELL SYSTEM

CROSS-REFERENCE TO RELATED APPLICATIONS

This application is a 371 of PCT/NL2011/050486, filed Jul. 6, 2011, which claims the benefit of European Patent Application No. 10168610.3, filed Jul. 6, 2010, the contents of each of which are incorporated herein by reference.

FIELD

The present invention is in the field of means for cell culture and more specifically in the field of means for culturing three dimensional tissue constructs. The present invention is also in the field of microwell systems as testing tools in analytical research and testing laboratories.

BACKGROUND

Culturing cells on flat plastic ware results in artificial two-dimensional sheets of cells. Normal cells in the human body experience a three-dimensional (3D) environment, completely surrounded by other cells, membranes, fibrous layers and adhesion proteins. Many whole cell-based assays in use today rely on flat, two-dimensional (2D) glass or plastic substrates that may not produce results characteristic of in vivo conditions. The value of 2D cellular assays is limited, because these assays do not mimic fully the response of cells in the 3D milieu present in a tissue in vivo. This may cause a lack of predictability of such 2D assays.

Various methods and materials have been studied for creating microenvironments. These efforts have so far been unpredictable, which indicates that not all relevant parameters which influence the development of 3D structures under culturing conditions are fully understood.

A system has been described wherein 3D synthetic polymer scaffolds are incorporated into standard cell culture dishes which support the formation of 3D cultures (Ke Cheng et al., Biomaterials 29 (2008), 2802-2812). These assays require 3D cell based vessels, which are fabricated by casting a thin layer of porous polymer scaffolds onto the glass bottom of a regular cell culture vessel. The 3D scaffolds are fixed on the vessels. With the aid of liquid handling robots, this 3D vessel fabrication can be applied to modify most currently available 2D cell culture vessels, such as 24-well-, 96 well- and 384-well plates for 3D cell culture and cell-based assay usage. A disadvantage of this approach is the dependency on existing well plates having a glass bottom. Moreover, these assays require many cells per well, a relatively large amount of medium and therefore also a large amount of test compounds.

It is therefore an objective of the invention to provide a multiwell system which has the following advantages:
- Requires a minimum amount of test compounds and cells
- Is suitable for high throughput screening
- Enables 3D tissue culture formation

SUMMARY OF THE INVENTION

The invention therefore provides a multiwell system, comprising wells having a volume between 0.125 and 4.0 mm$^3$.

More preferably, said multiwell system is made of a biocompatible material. More preferably, said biocompatible material is a material which has been approved for use in an animal by a legal authority, preferably the FDA or EMEA. More preferably, said biocompatible material is polylactic acid, PEOT/PBT. In a preferred embodiment, said wells have an inner diameter larger than 0.5 mm. Preferably, said multiwell system comprises at least one well comprising a 3D tissue construct.

The invention further provides a method for producing a multiwell system according to the invention, wherein said multiwell system is produced by extrusion. Preferably said methods comprises steps of melting said biocompatible material in a thermal jacket; extruding the melted biocompatible material under pressure through a nozzle to form a plotted fiber; step b is repeated, thereby depositing a subsequent plotted fiber in parallel at a distance of between 0.125 and 4.0 mm next to the last deposited fiber until a layer is formed; a subsequent layer is deposited on the previous layer, wherein the fibers forming said subsequent layer are deposited at an angle preferably between 10 and 90 degrees relative to the fibers of the previous layer; repeating said step wherein said subsequent layer is deposited until the desired height is achieved.

The invention further provides a method for preparing a 3D tissue construct from cells, comprising steps of introducing a medium comprising cells in a multiwell system according to the invention and culturing the cells to obtain a 3D tissue construct. Preferably, the medium comprises at least 4000 cells. Any cells which are in vivo capable of forming 3 dimensional (3D) tissues may be used. Preferably, the cells are stem cells, preferably human Mesenchymal Stem Cells (hMSC), or chondrocytes.

In a preferred embodiment, said cells are of a first type of cells and wherein cells of a second type are introduced in the well and cocultured with the cells of the first cell type in step b, wherein the cells of the second type stimulate the growth of cells of the first type in the formation of said 3D tissue construct.

Preferably, 3D tissue constructs are formed in 2 or more wells of the multiwell system and wherein different culturing conditions are applied to the 2 or more wells.

Preferably, the multiwell system is implanted in a pocket of a suitable animal. In some embodiments, the system is implanted in a human. In some embodiments, the system is implanted into a non-human animal.

The invention further provides an animal, preferably a non-human animal, comprising a multiwell system according to the invention, wherein said multiwell system comprises cells.

DETAILED DESCRIPTION OF THE DRAWINGS

FIG. 1 shows three examples of multiwell systems according to the invention wherein wells were designed in a matrix array (columns×rows). FIG. 1A represents a three-dimensional view of a 10×10 array. FIG. 1B shows a view from above of the a multiwell system with rectangular wells. FIG. 1C shows the cross-section of a multiwell design where bottom and sides are closed, and top is opened. FIG. 1D represents the cross section of another multiwell design consisting of a double-sided 10×10 array. The wells are rectangular and have an open top and bottom and a layer of material in the middle. FIG. 1E shows the cross section of a third multiwell design combined with electrospinning. The bottom and sides of each well are closed and a layer of electrospun fibers is introduced as a middle layer. The measurements indicated are in micrometers. These measurements and designs are only illustrative and should not be interpreted as limiting the scope of the invention.

FIG. 2 shows a method for producing a multiwell system according to the invention. In this figure, the process of extrusion is shown. In FIG. 2A is shown how a plotted fiber is extruded. A material is melted in a thermal jacket (c) connected to a pressurized cap (b) and a heated syringe, and pressure (preferably around 4 bars) is applied through a nitrogen flow (a). This causes the material to flow and be extruded in the form of a fiber, resulting in a plotted fiber (e). A multitude of plotted fibers in parallel to each other in the same horizontal plane (in the Z axis) together form a layer. FIG. 2C shows different architectures as a result of varying the angles of the deposited fibers of a layer vis-a-vis the fibers of the previous layer. (i) and (k) are examples of rectangular architectures, whereas (j) and (l) are examples of architectures obtained when the angles of the fibers are 45°.

Figure 3:
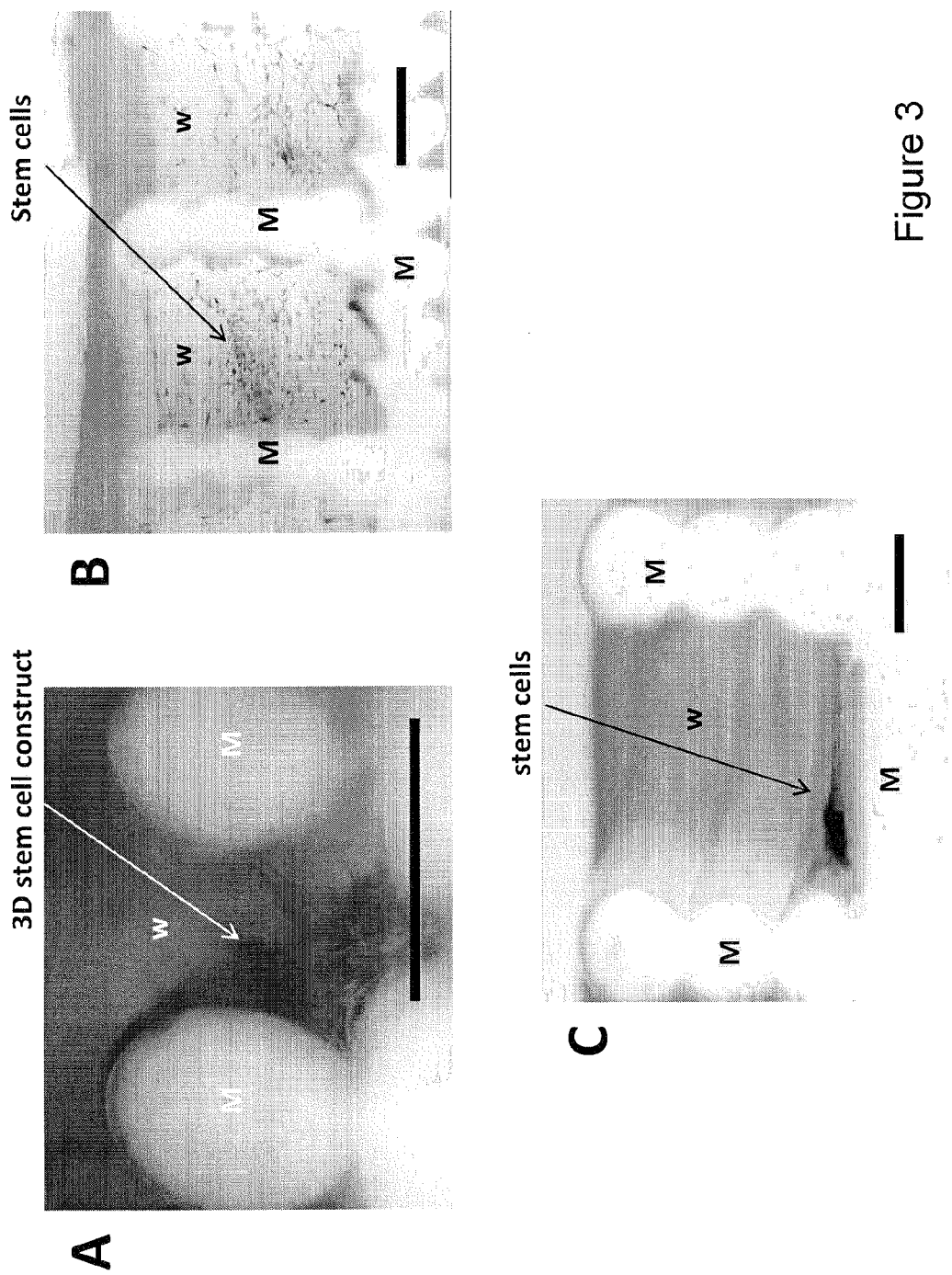

FIG. 3 shows the importance of the well dimensions. The well dimensions were selected based on two criteria: The first is the ability of human mesenchymal stem cells (hMSCs) to form a three-dimensional construct. The second is the ease of manipulation of wells of the multiwell system by user. On figures A, B and C, "M" stands for material, "w" stands for well, stem cells were stained blue. Scale bars equal 0.5 mm. Every figure shows hMSCs in culture for two days in wells of different XYZ axis dimensions: (A) 0.5 mm×0.5 mm×0.5 mm, (B) 1 mm×1 mm×1.8 mm, (C) 1.5 mm×1.5 mm×1.8 mm. Each well was seeded with 25,0000 hMSCs/well. Based on figures A, B and C, it was determined that: (A) hMSCs could form a 3D structure depending on culture time and well size, (B) Well size on figure B was the easiest to manipulate by users. The well size on figure B was designed based on the 2.5 µl pippette tip (Plastibrand, outer diameter 0.5 mm), which allowed us to put the tip inside of the well and place 0.8-1 µl cell suspension into each well. In addition, the design on figure B improved the visual and manual manipulation without the need of microscopes. Wells with a volume larger than 3 $mm^3$ were easier to manipulate, but required longer culturing time to obtain 3D constructs with the same number of hMSCs. Wells smaller than 0.25 $mm^3$ (FIG. 3A) were more difficult to manipulate. The optimal balance between, manipulation, number of cells required and culturing time was provided by the wells between 1.0 and 3.0 $mm^3$. In conclusion, wells on figure B (Approx. 1×1×1.8 mm) have the best manipulation characteristics and results in the most desirable culture time to induce hMSCs into 3D tissue constructs.

Figure 4:
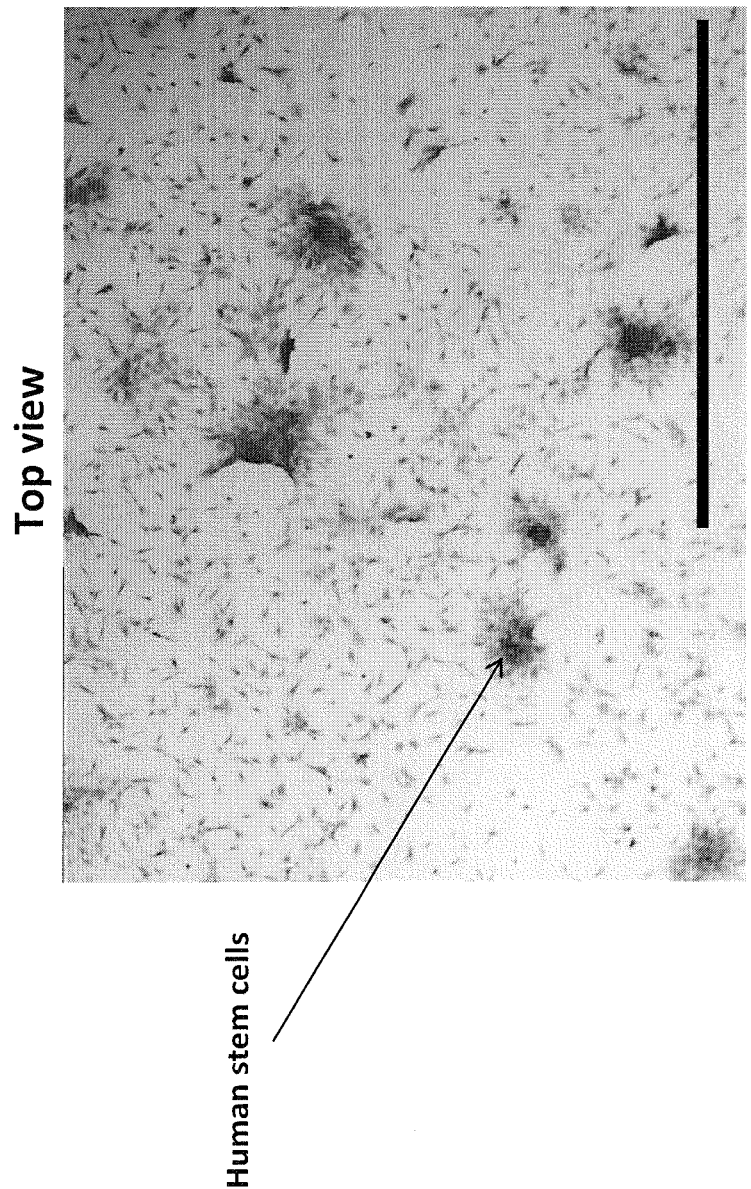

FIG. 4 shows hMSCs cultured for 10 days on a disc made of PEOT/PBT. In this experiment, 300,000 hMSCs were seeded per disc. This shows that no matter how long culturing time is, hMSCs do not form a 3D tissue construct. Bar equals 0.5 mm. hMSCs are stained blue (Methylene blue).

Figure 5:
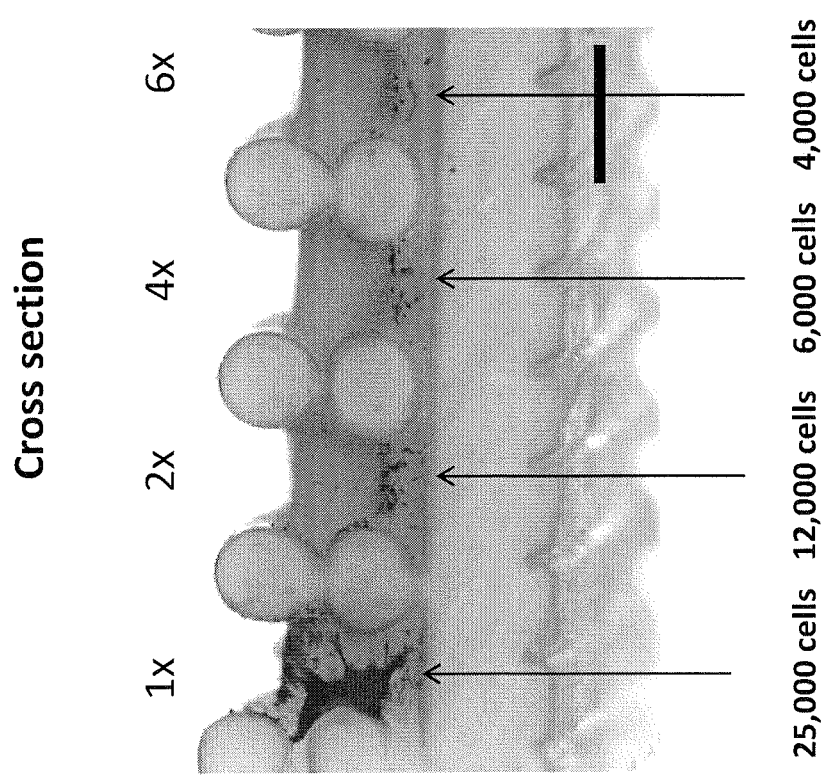

FIG. 5 shows the influence of the different number of cells (preferably) hMSCs were seeded into each well. This figure shows cell dilutions after 4 days in culture. 3D tissue constructs in wells are cell-number and time dependent. We used time-dependency to set experimental parameters to obtain 3D tissue constructs: 25,000 cells were the higher number of hMSCs seeded per well; hMSCs were cultured in wells for 4-7 days. Bar equals 0.5 mm.

FIG. 6 shows 3D hMSCs constructs in wells initially seeded with 25,000 and 12,000 cells/well after 5 days in culture. Figures A-B show cell nuclei staining and Figures C-D show staining of proliferating cells. This shows how we can use time and cell numbers to determine the size and state of 3D hMSCs constructs in each well. Scale bar: 100 µm.

Figure 7:
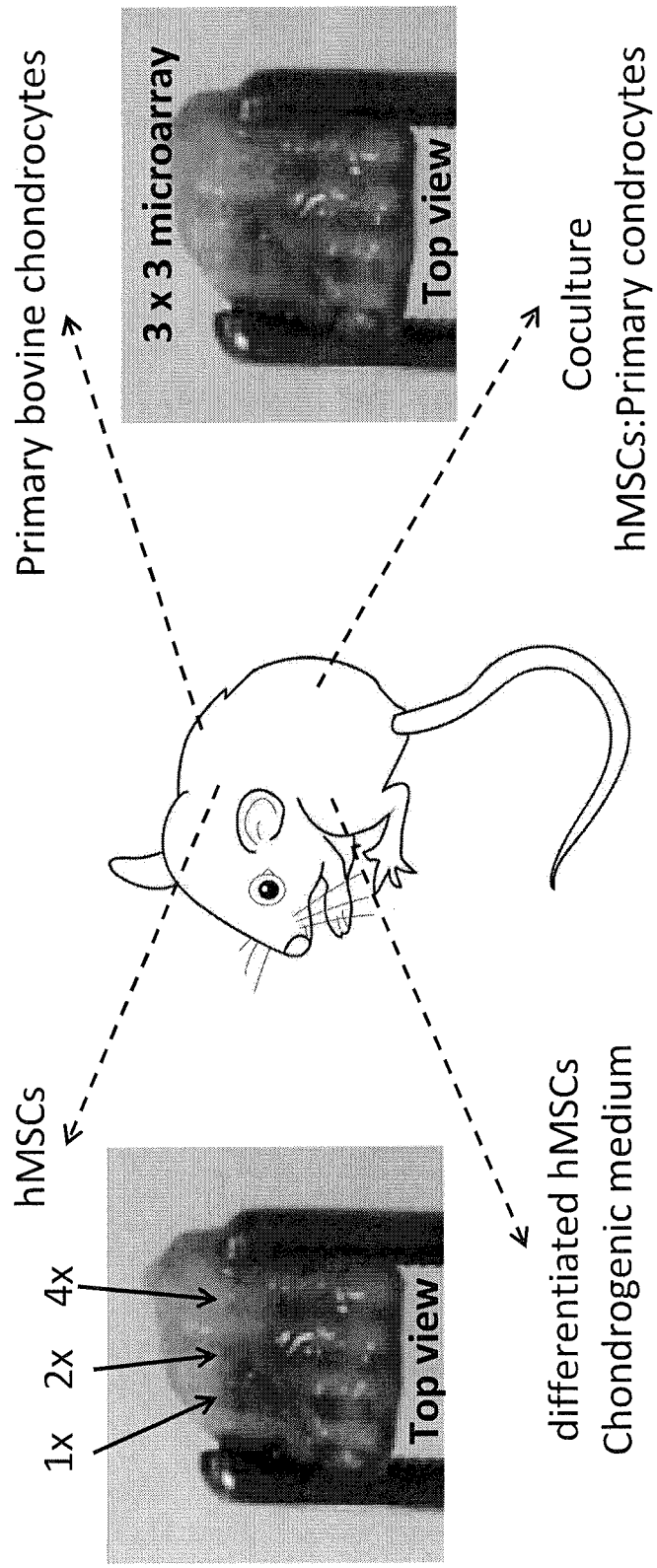

FIG. 7 illustrates a method for culturing cells in an animal according to the invention. We made a (3×3) rectangular shaped multiwell system according to the invention with wells of 1 mm×1 mm×2 mm and seeded three different cell types and a coculture in four multiwell systems for a total of four different culture conditions. For each cell type, 3 cell dilutions were seeded: 1×, 2× and 4× for a total of three different dilutions in triplicates. 1× equals 25,000 cells. The coculture was seeded in each of the three columns with hMSCs:primary bovine chondrocytes ratios of 0:1, 0.5:0.5, and 1:0. After 4 days in vitro culture, each multiwell system having the different dilutions were implanted in one of four pockets/mouse in a total of 10 mice. Therefore, in each mouse pocket, we had one culture condition and 3 dilutions.

Figure 8:
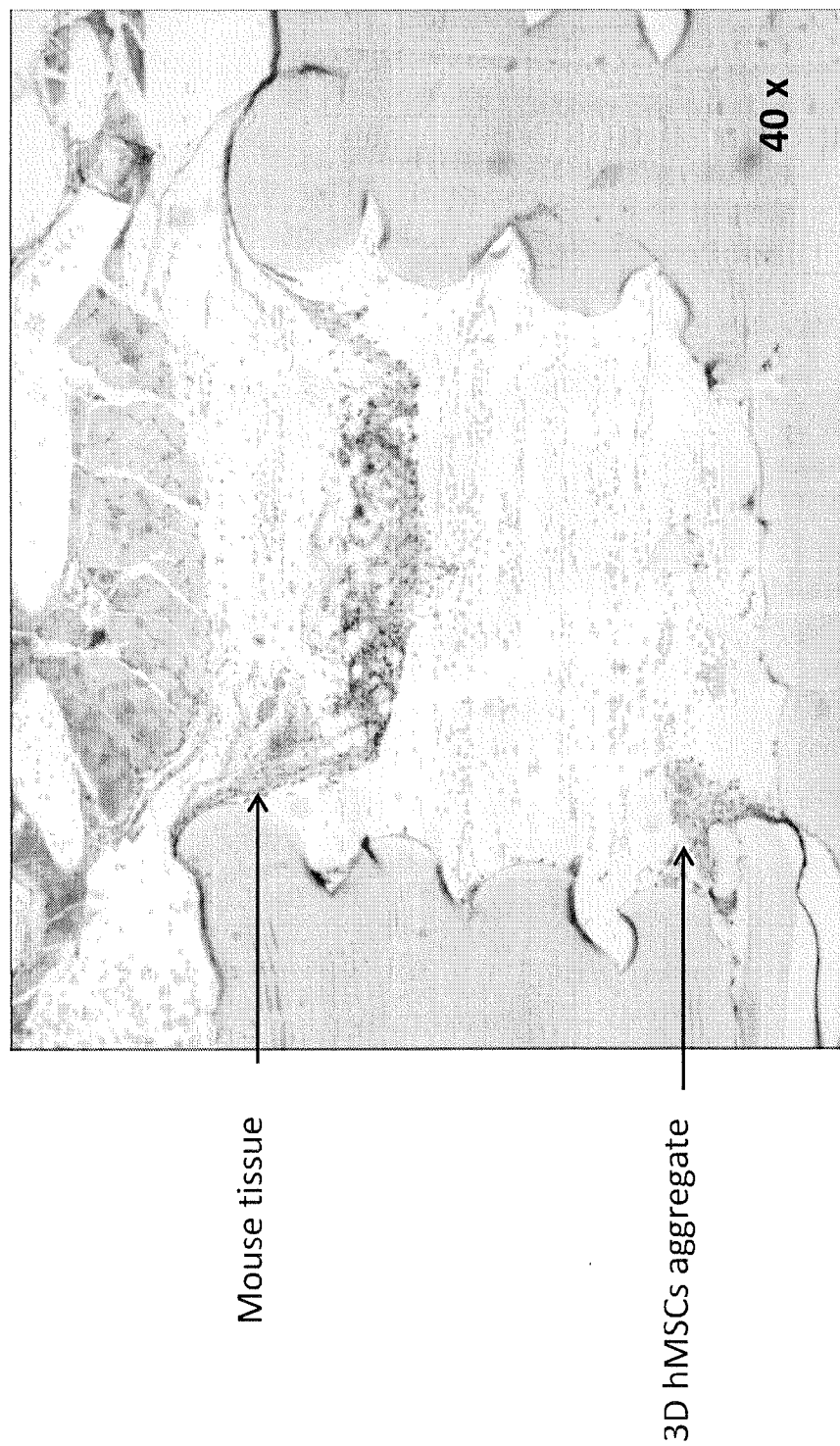

FIG. 8 shows one well channel seeded with 12,500 hMSCs, implanted in a mouse and explanted (removed) after one month. This shows how mouse tissue penetrates well after 1 month of implantation. Staining is performed using Masson's Trichrome.

Figure 9:
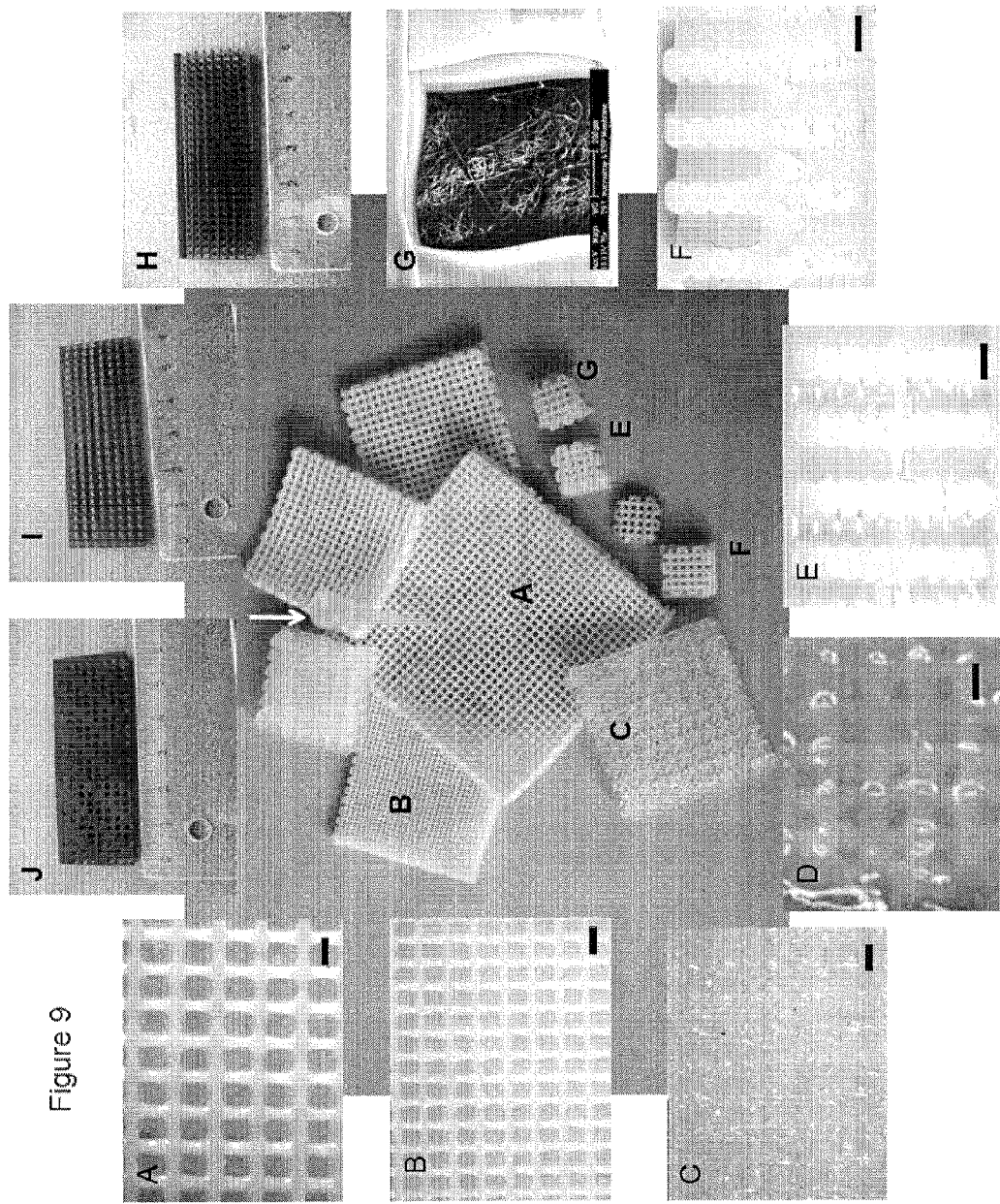

FIG. 9 shows that Multiwell systems can be made of different materials and with different architectures. White arrow points to pipette tip size that fits into a well. A: Top view of 1024 wells in a 32×32 array made of PEOT/PBT of 300/55/45 composition. B: Top view of 100 wells in a 10×10 array made of PEOT/PBT of 1000/70/30 composition. C: Top view of 100 wells in a 10×10 array made of poly lactic acid. D: Top view of 100 wells in a 10×10 array made of alginate (in PBS). E: Cross section of a double array with polymer layer in between and opened bottom and top sides made of 300/55/45 composition of PEOT/PBT. F: Cross section of wells made of PEOT/PBT 300/55/45 with a porous layer in the middle. Closed bottom layer and an opened top. Scale bar: 1 mm. G: Top view of a well composed of PEOT/PBT of 300/55/45. The sides and first layer were 3D-printed and a layer of electrospun fibers was introduced in the middle of the well's height. H: Rectangular wells produced by stereolithography. I: Round wells produced by stereolithography. J: Round wells patterned across the XY axis of the macroarray and produced with stereolithography.

Figure 10:
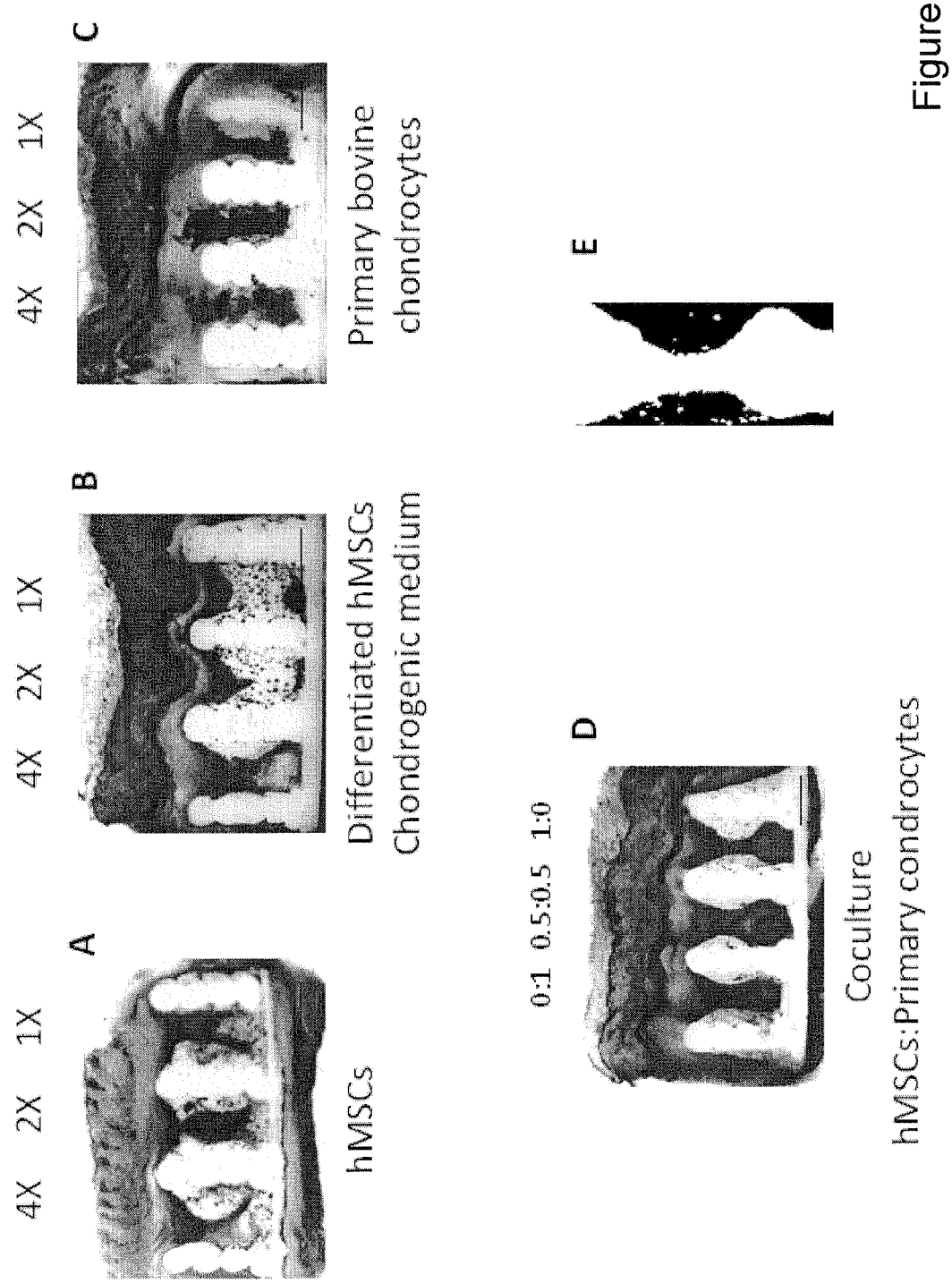

FIG. 10 shows the results of four conditions seeded in 3×3 macroarray and implanted in mice. 1× was equivalent to 25,000 cells seeded per well. 25,000 cells were the highest number of cells seeded in a well. A: hMSCs. B: Differentiated hMSCs C: PBCs D: coculture hMSCs:PBCs in three ratios 0:1, 0.5:0.5, 1:0. E: Example of image used for tissue area quantification within each well. The image fits into the area contained in one well using the macrowell material as reference. Scale bar: 1 mm.

Figure 11:
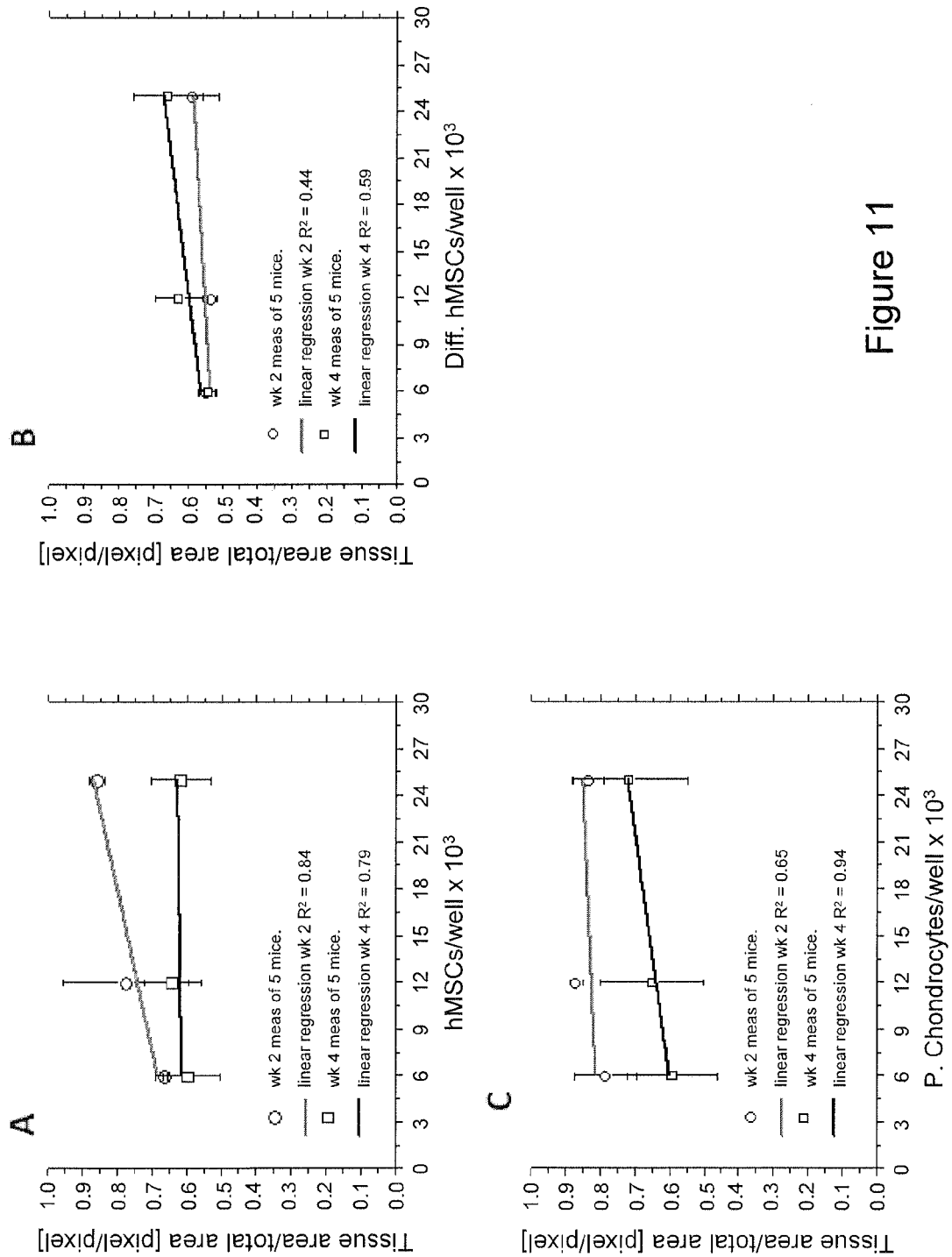

FIG. 11 shows the linear regression analysis of tissue area vs. cell numbers on weeks 2 and 4. A: hMSCs B: Differentiated hMSCs. C: Primary chondrocytes. Statistical significance $p<0.05$.

Figure 12:
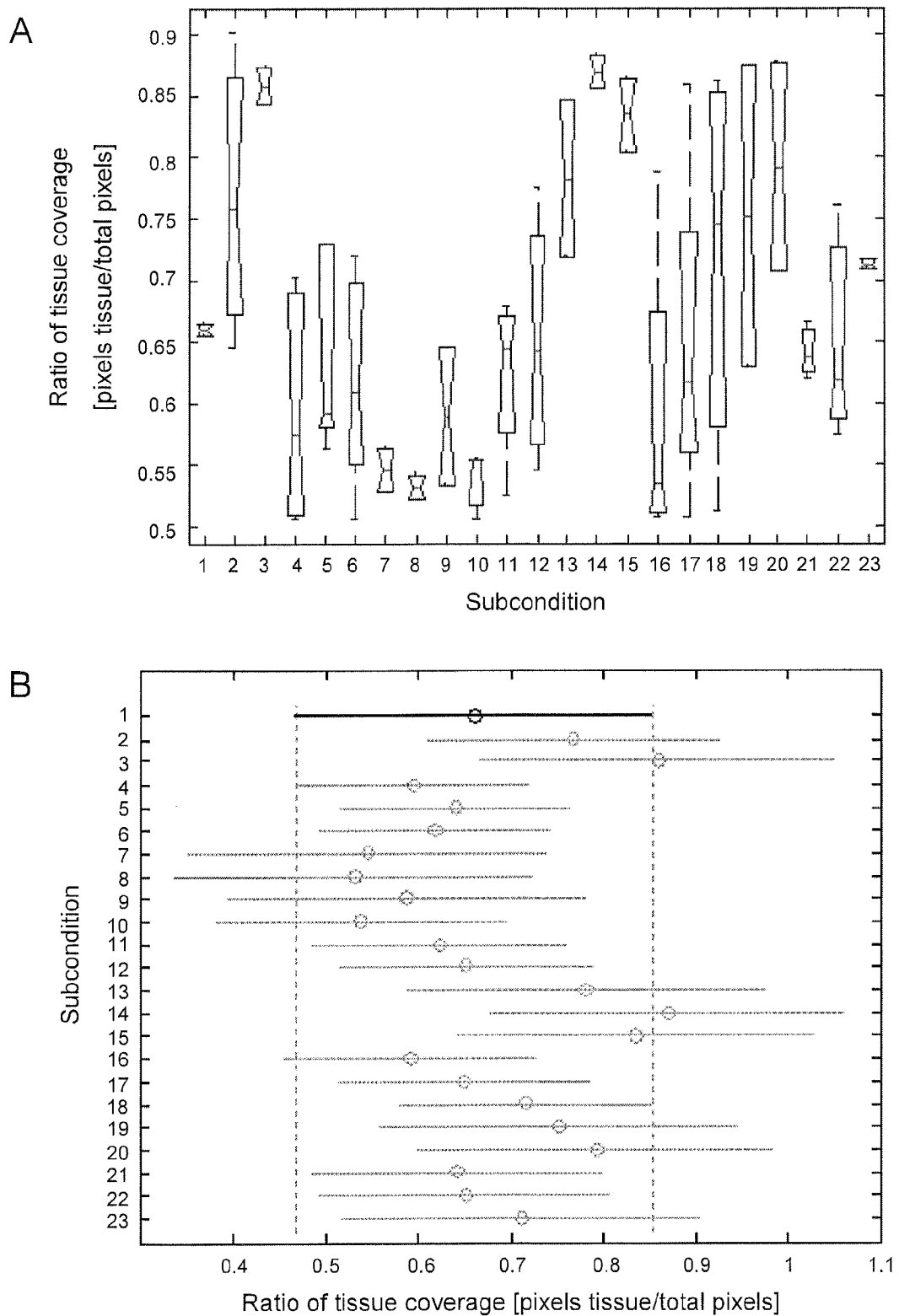

FIG. 12 shows the statistical analysis of tissue area quantification in each well of all sub-conditions implanted. Each sub-condition is represented by a number referenced in table 1. A: ANOVA box plot of all sub-conditions. B: Multiple comparison test of means of all sub-conditions with each other according to ANOVA statistics and their 95% confidence interval.

Figure 13:
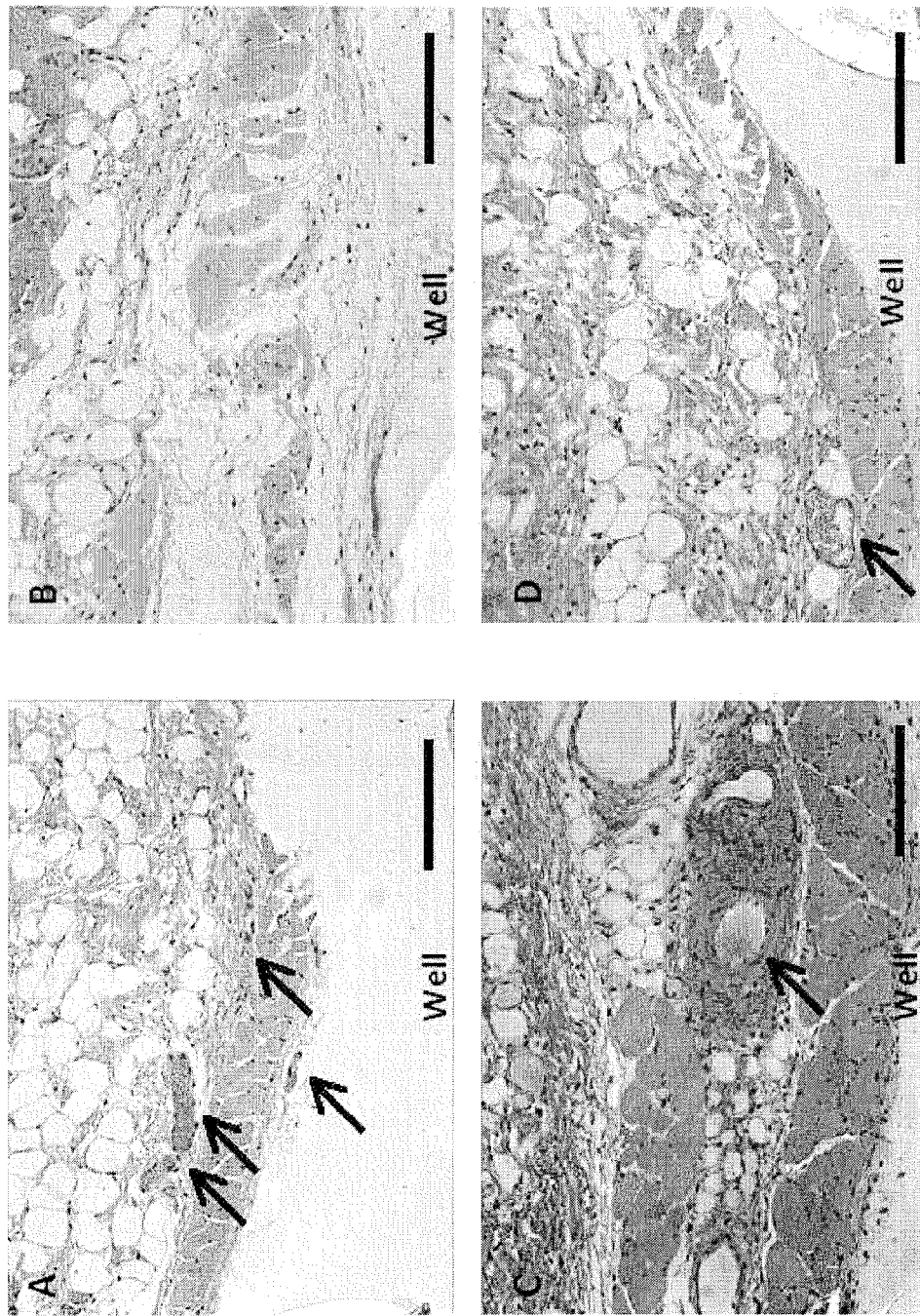

FIG. 13 shows haematoxylin and eosin staining of representative sections of host tissue above well macroarrays after 1 month implantation. 100× magnification. Arrows point to vessel lumens. A: hMSCs. B: Differentiated hMSCs C: Primary Chondrocytes. D: Coculture hMSCs:Primary Chondrocytes. Scale bar: 100 µm.

Figure 14:
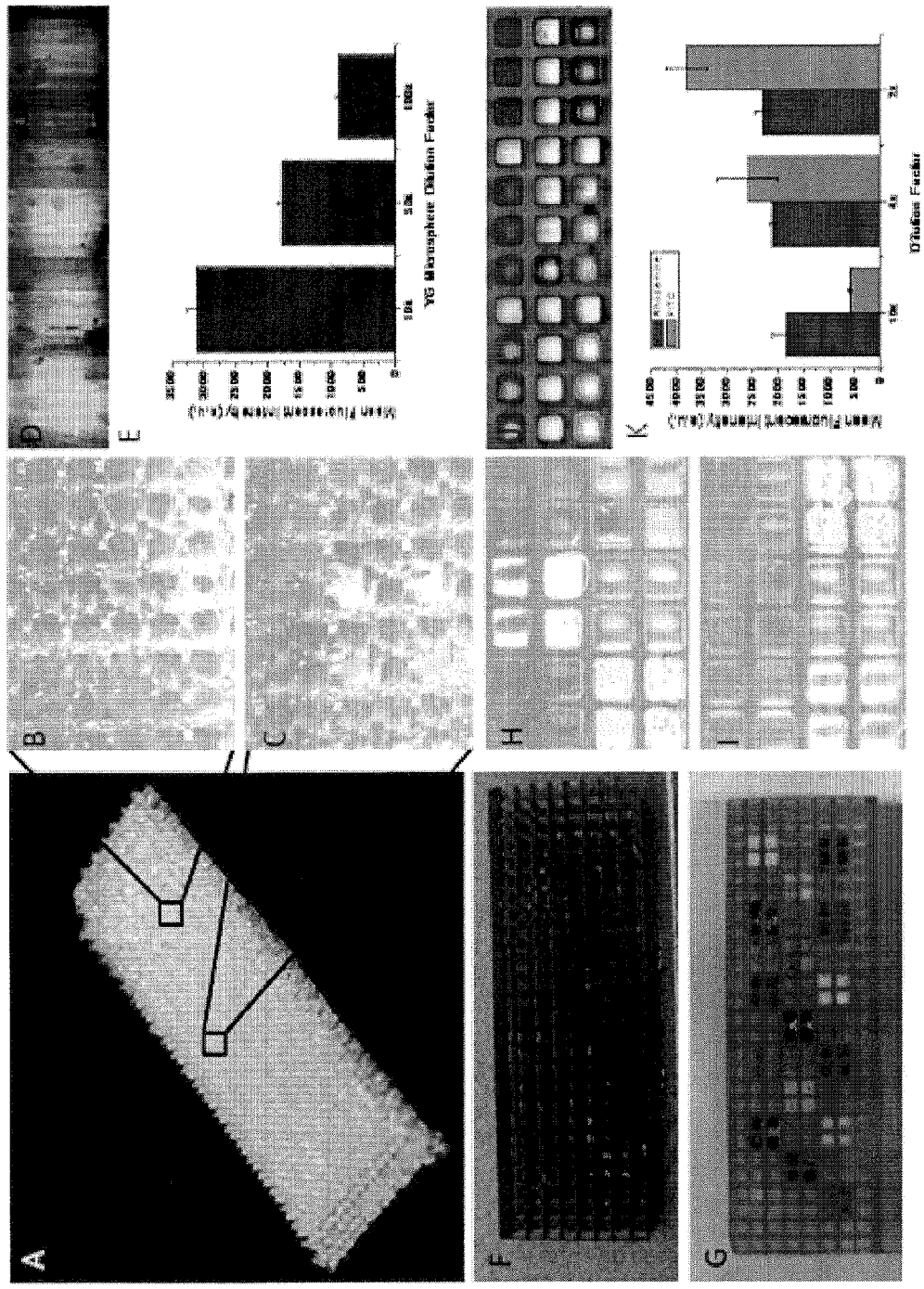

FIG. 14. 3D HTS (three-dimensional high throughput screening) system with dimensions customized to fit automatic confocal light microscopy analysis fabricated by (A) fused deposition modeling and (F, G) stereolithography. Inserts (B, C, H, I) show that for both systems it is possible to detect dyes of different colors (red, blue, yellow, purple, white) corresponding to different wavelengths, thereby demonstrating that this system can be used to analyze specific cellular response in multiplex analysis by e.g. fluorescent markers with specific wavelength excitations. (D) Fluorescent microspheres (YG: λ=441-486 nm) seeded in the multiwell system can be detected and (D) quantified at different dilutions with an automatic confocal light microscope. Similarly, (J, K) rhodamine red and FITC have been detected and quantified at different dilution concentrations. Rhodamine and FITC concentrations have been varied in opposite directions in order to remove potential arbitrary biases.

Figure 15:
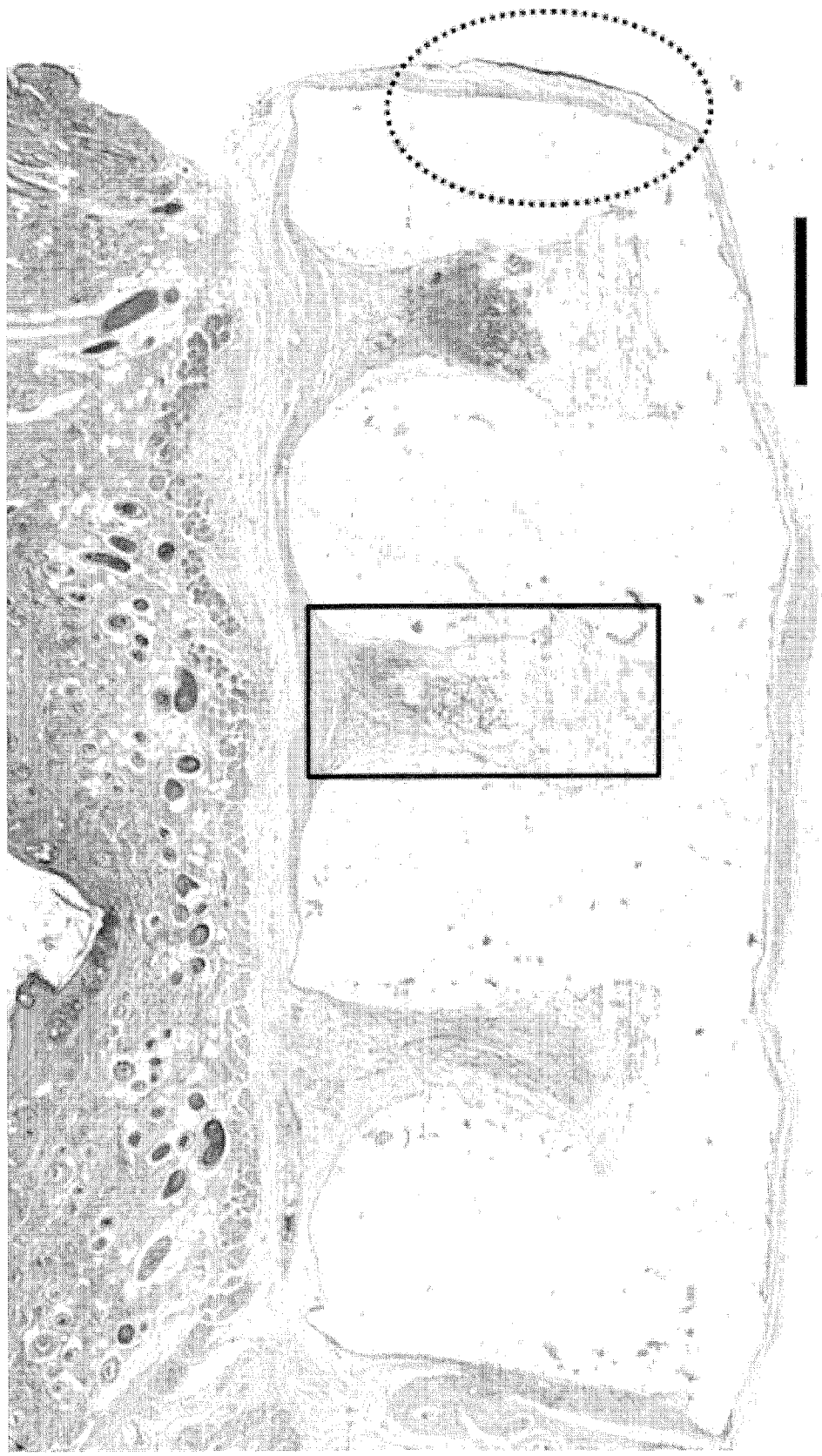

FIG. 15. Cross section of the explanted 3D HTS system showing three wells or sub-conditions contained within each macroarray. Mouse tissue penetration can be observed in each well. Slides were stained with Haematoxylin and counter-stained with eosin. Cytoplasm (Red) and Nuclei (Dark blue). The slides showed potential differences in the tissue penetration depending on the cells seeded in each well. To quantify the tissue penetration, a rectangle of the dimensions of each well was drawn. By calculating the tissue area contained within each rectangle, the percent area of tissue in each well/sub-condition was obtained. To be able to pinpoint sub-conditions after processing the samples, one side of the macroarray was stained with India ink, which was visible (inside the dotted circle) in the slides. Scale bar: 1 mm.

FIG. 16. The tissue percent area for each sub-condition for two mice: one from week 2 and one from week 4. The 3D bars show trends: higher number of cells seeded means more tissue percent area in a well. A: hMSCs dilutions and control (empty 3D HTS system). B: Chondrocytes dilutions and control. C: Co-culture of hMSCs and chondrocytes and control.

Figure 17:
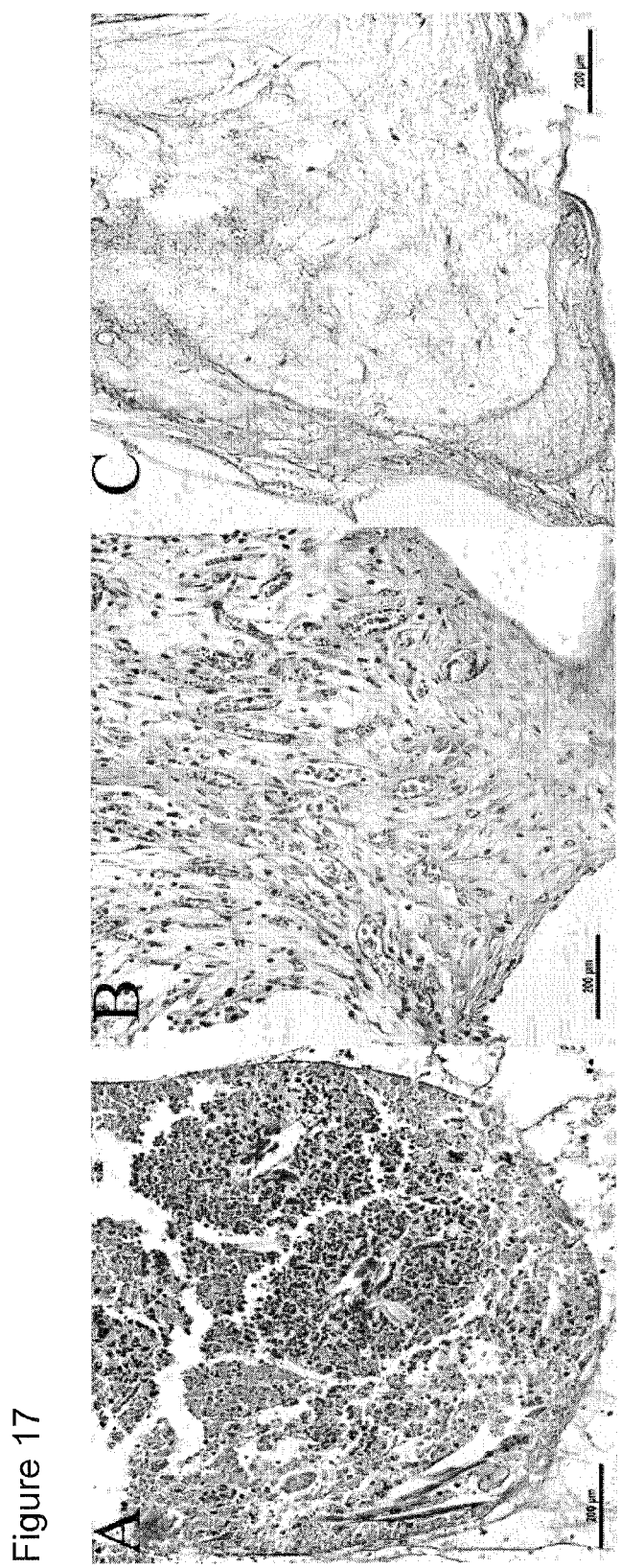

FIG. 17. Higher hMSCs numbers promote tissue organization in the wells. Slides stained with Masson's tri-chrome: Keratin (Red), Collagen (Blue) and nuclei (dark brown or black). A: Control shows mouse muscle tissue in the wells without cells. B: hMSCs 1× dilution (~25,000 cells) on week 2 show tissue organization: Note the alignment of collagen fibers and blood vessel distribution. C: hMSCs 2× dilution (~12,500 cells) on week 4 shows tissue organization: Collagen fibers are aligned Scale bars: 200 µm.

Figure 18:
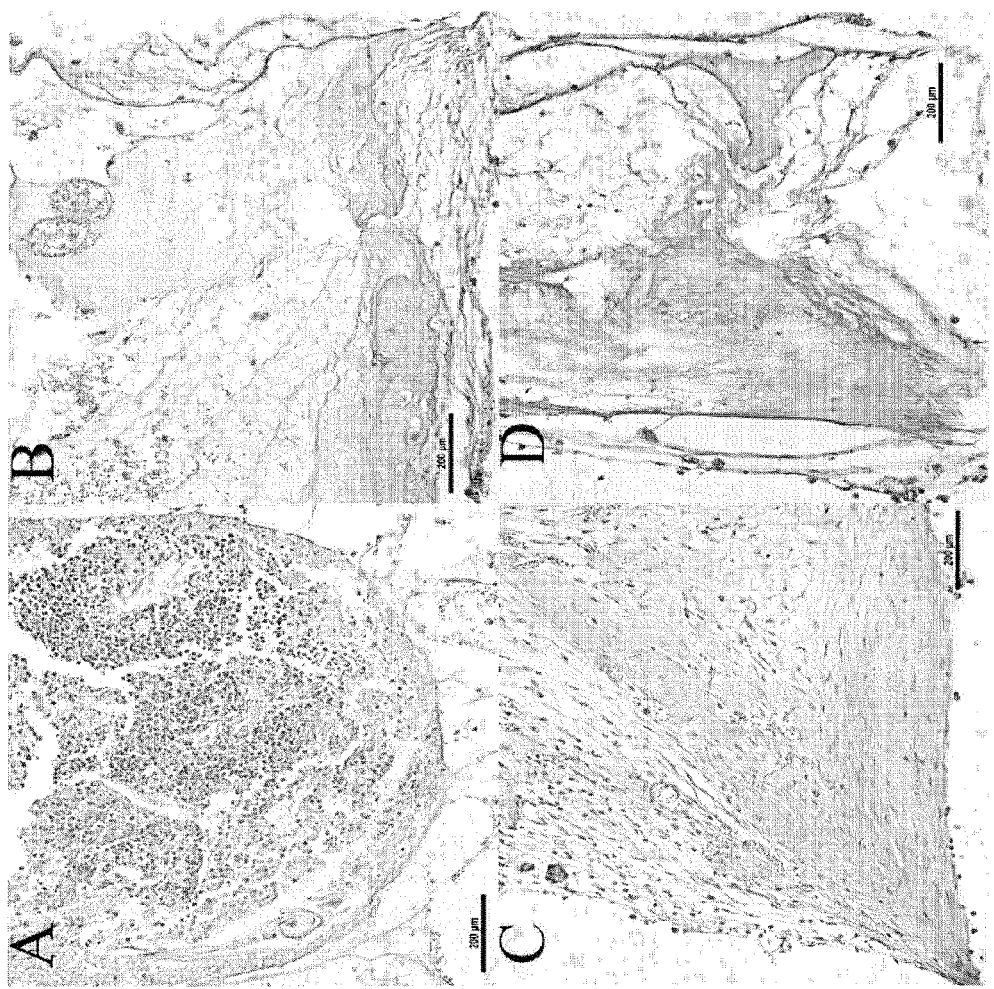

FIG. 18. Cartilage regeneration according to conditions that show glucosaminoglycans (GAG) formation. Slides were stained with Alcian blue and counterstained with Eosin: GAG (Blue) and cytoplasm (Red). A: Controls were not positive for GAG in mouse tissue that penetrated in the well. B: Chondrocytes 1× dilution (~25,000 cells) was not positive for GAG. C: Coculture of hMSCs:Chondrocytes at 20:80 ratio; a total of 25,000 cells were seeded in the well. This sub-condition was not positive for GAG. D: Coculture of hMSCs: Chondrocytes at 80:20 ratio. A total of 25,000 cells were seeded in the well. This sub-condition was positive for GAG. Scale bars: 200 µm.

DETAILED DESCRIPTION

Definitions

The term "multiwell system" refers to an array of sample wells located on a substantially flat surface. Multiwell systems may comprise any number of separate sample wells. A multiwall system according to the invention comprises at least 3 wells, preferably at least 9 wells. Common examples of multiwell systems include 96 and 384 well systems. The term "multiwell system" can be used interchangeably with the term "microwell plate", "well macroarray" or "microplate".

The term "well" as used herein denotes a compartment or recessed area. Preferably said well is separated from another well by a lateral wall which prevents mixing the content of said well with another well. Preferably, said well has a closed bottom.

The term "biocompatible" as used herein refers to the characteristic of the material which enables the material to be implanted in an animal, without being toxic to the animal or invoking an immune response in the animal.

The term "inner diameter of a well" as used herein refers to the diameter of said well as can be determined by establishing the maximum diameter of a cylindrical form which can be inserted into said well.

The term "3D tissue construct" as used herein refers to a multitude of cells which form a 3 dimensional tissue. Preferably, said 3D tissue construct comprises at least 2, 3, 4, 5 or 6 cells grow on top of each other. Preferably, said 3D tissue construct comprises at least 2, 3, 4, 5 or 6 cell layers. Preferably, said cells forming said 3D tissue do not form a suspension and preferably have an adherent growth pattern.

The term "medium" as used herein refers to a fluid which can be used to keep, store or culture cells without damaging the integrity of cells.

The term "pocket" refers to a site within an animal body which is suitable for implanting a multiwell system. Preferably, said pocket is a subcutaneous site.

Embodiments

The invention is based on the surprising finding that cells, which in vivo are capable of forming 3D tissues, but when cultured in vitro in a petri dish or a regular culture flask only produce 2D layers, form 3D tissue constructs when cultured in wells having a volume between 0.125 and 4.0 mm$^3$. Normally, cells do not form 3D tissue constructs in multiwell systems, no matter how long they are cultured (see also FIG. 4), unless such multiwell systems are prepared by incorporating 3D synthetic polymer scaffolds. Surprisingly, the inventors have demonstrated that very small well volumes induce the formation of 3D tissue constructs. The multiwell systems provided herein therefore preferably do not comprise 3D synthetic polymer scaffolds.

Multiwell System

The invention provides a multiwell system comprising wells having a volume between 0.125 and 4.0 mm$^3$. An advantage of the microwell system according to the invention is that the volume of reagents required for culturing is greatly reduced, thereby saving costs. It is essential that the multiwell system is suitable for cell culturing. In a preferred embodiment, said multiwell system is made of a biocompatible material, which allows said multiwell system to be implanted in an animal. Any biocompatible material can be used, including thermoplastic polymers, metals and hydrogels. However, it is a great advantage if the biocompatible material is a material which is approved by a legal authority, preferably the FDA or EMEA for use in an animal. In a preferred embodiment, the biocompatible material is alginate (see FIG. 9D). More preferably, said biocompatible material is polylactic acid or PEOT/PBT (obtainable from IsoTis S.A., Bilthoven, The Netherlands). In case PEOT/PBT is used, the most preferred compositions are PEOT/PBT of 300/55/45 and 1000/70/30 compositions, because they gave the best results. In a preferred embodiment, said wells have an inner diameter larger than 0.5 mm. An advantage thereof is that some standard micropipette tips have an outer diameter of 0.5 mm, which therefore fit perfectly in such wells.

In certain embodiments, said microwell system is implanted in an animal, as will be described hereunder. Depending on the size of the animal and the size of the transplantation pockets therein, the maximum number of wells and therefore the maximum number of culture conditions which can be tested may differ. Therefore, the dimensions of said multiwell system is preferably adjusted in order to fit into an implantation pocket of a specific animal. A suitable multiwell system which can be transplanted in a transplantation pocket of a mouse, is preferably smaller than 10×10 mm. A suitable multiwell system which can be transplanted in a transplantation pocket of a rat, is preferably smaller than 20×20 mm. A suitable multiwell system which can be transplanted in a transplantation pocket of a rabbit, is preferably smaller than 30×30 mm. A suitable multiwell system which can be transplanted in a transplantation pocket of a goat, is preferably smaller than 50×50 mm.

A multiwell system having 16 wells or fewer is preferred when said multiwell system is transplanted in a transplantation pocket of a mouse. A multiwell system having 2000 wells or fewer is preferred when said multiwell system is transplanted in a transplantation pocket of a rabbit. A multiwell system having 12000 wells or fewer is preferred when said multiwell system is transplanted in a transplantation pocket of a goat.

Preferably, the height of said multiwell system is between 0.4 and 8 mm. Preferably the maximal height is 8.0, 4.0, 3.5 or 3.0 mm. Preferred outer dimensions of the multiwell system are 75×25×6 mm (length×width×height). An advantage thereof is that the outer dimensions of 3D multiwell system having these dimensions are adapted to fit into the holder of an automatic confocal light microscope. Preferably, the well volume is greater than 0.05 microliter, greater than 0.1 microliter, and more preferably greater than 1.0 microliter.

Preferably, the walls of the wells are more than 50 microns thick. The thickness of the well walls provides mechanical stability allowing the multiwell plates to withstand the forces exerted by tissue in vivo. Preferably, the well walls are at least 60 microns, at least 70 microns, at least 80 microns, at least 90 microns, 100 microns, at least 1 mm, or at least 2 mm thick. Preferably, the well walls having a minimum thickness as described herein are less than 3 mm thick. Preferably, the walls are between 60 microns and 3 mm thick, more preferably between 100 microns and 1 mm thick.

Preferably, said multiwell system comprises at least one well comprising a 3D tissue construct. Preferably, said multiwell system comprises multiple wells comprising a 3D tissue construct. An advantage thereof is that such multiwell systems comprising multiple wells having said 3D tissue construct can suitably be used to test different variables, including testing different compounds or culturing conditions. Of course, preferably more wells are used to test more different test variables simultaneously. In a preferred embodiment, at least, 2, 3, 4, 5, 6, 7, 8, 9, 10, 15, 20 or 25 wells comprising a 3D tissue construct are exposed to different culture conditions or to different compositions of the culture medium. In a preferred embodiment, said composition of the culture medium is different, because at least a chemical compound is present in a well which is absent in other wells of said multiwell system.

The multiwell system can suitably be used to test virtually any detectable effect of a compound on a cell in a 3D tissue construct. The toxicity of a compound can be determined by comparing cell death in a 3D tissue construct compared to a 3D tissue construct which has not been exposed to said compound. In another embodiment the level of a protein, nucleic acid or metabolite is determined in a cell of said 3D tissue construct which has been exposed to a certain compound or culturing condition and compared to the level of the same protein, nucleic acid or metabolite in a cell of said 3D tissue construct which has not been exposed. It is of course also within the scope of the present invention to test an effect of a compound of culturing condition during the formation of a 3D tissue construct.

Uses of the Multiwell System

Said multiwell system allows performing thousands of experiments within a single vertebrate animal and offers the extraordinary possibility to screen multiple conditions in vivo. The inventors evaluated first in vitro the effect of well sizes on hMSCs growth, and organization, and on tissue development by creating 3D well macroarrays of PEOT/PBT and seeding cells (preferably hMSCs) in them. They concluded that well dimensions, cell numbers, and culture time were the most important parameters to control tissue culture within the multiwell system. Concentrating cells in a well significantly reduced the need for cell expansion. In addition, using 4000-25000, more preferably between 6000-25000, and most preferably between 12000-25000 hMSCs, 3D hMSCs aggregates of different sizes could be produced by adjusting the culture time. Wells having a volume of approximately 1.8 $mm^3$ were optimal to seed, culture and manually manipulate multiwell systems in vitro with 25,000 hMSCs or less.

The size of wells developed in the multiwell system according to the invention falls between the sizes of currently available microfabricated high throughput systems and conventional culture plate arrays. The size of the multiwell system according to the invention combines two advantages: (i) less resources are used. For example, low cell numbers are used to seed each well; (ii) manipulation of said multiwell system is possible using standard laboratory equipment. For instance, the use of standard pipette tips is possible. The multiwell system according to the invention has the potential to house thousands of wells within one multiwell system. The microwell system according to the invention can be also created in a custom shape that allows insertion in already commercially available automated microscopes that allows also automated analysis. Another advantage which this multiwell system according to the invention has is that its use results in the reduction of the number of animals used in in vivo experiments. This is achieved by making said multiwell system of biocompatible polymers and by adjusting well numbers and multiwell system size to the implantation site of the test animal.

The multiwell system used in vivo experiments was a 3×3 well multiwell system. Said multiwell system was subcutaneously implanted in a mouse to screen the effect on tissue formation of having different cell numbers per well in one mouse pocket. Three cell types were tested. In addition, three different ratios of hMSCs:primary chondrocytes coculture were implanted. Trend analysis with linear regression showed that there was a correlation between tissue area ratio vs. cell number for hMSCs at week 2 and for primary chondrocytes at week 4. This indicated that wells with high cell numbers produced wells with a higher tissue coverage ratio. Even though there were trends detected, ANOVA analysis of the tissue coverage ratio did not vary significantly between culture conditions. This suggests that culture conditions tested were not extreme enough to result in a significant difference in tissue coverage of the well with the markers analyzed. Interestingly, multiwell systems comprising hMSCs displayed the presence of vascular lumens of larger size and in higher numbers than multiwell systems with chondrocytes, or differentiated hMSCs. Vessels were observed repeatedly in microwell systems seeded with hMSCs.

Using conventional microplates, performing tissue screening analysis of the same cell numbers and co-culture ratios would have required 3 times the number of animals as each culture condition (or variable to be tested) would have had to be tested separately. The multiwell systems tested herein were made of PEOT/PBT. As shown in FIG. 9, many other materials could be also used, which underlines the versatility of said multiwell system. The use of multiwell systems according to the invention drastically reduces vertebrate animal lives and costs in pharmaceutical, toxicological, chemical, and disease screening, while allowing for the first time to perform such screening in true three-dimensional tissues. It is anticipated that this technology will contribute to advance society health conditions.

Methods for Producing the Multiwell System

The multiwell system according to the invention can be made using any suitable method, like by casting, etching, embossing, extrusion etc. Furthermore, any rapid prototyping method can be used. Rapid prototyping is the automatic construction of physical objects using additive manufacturing technology. Preferred methods of rapid prototyping include selective laser sintering (SLS), which uses thermoplastics or metals powders, fused deposition modeling (FDM), which uses thermoplastics or eutectic metals, stereolithography (SLA), using photopolymers, electron beam melting (EBM), using titanium alloys and 3D printing (3DP), which can be used with various materials. These methods employ different technical measures to solidify material, which can be used to prepare said multiwell system. Using stereolithography, a photosensible polymer in a liquid state is solidified by selective exposure to specific light wavelengths (FIG. 9H-J). Using selective laser sintering a powder of a biocompatible material is selectively hit by a laser beam that partially melts the powder, resulting in the formation of a solid structure. 3D printing is a form of additive manufacturing technology where a three dimensional object is created by successive layers of material.

Preferably a method for producing a multiwell system according to the invention is used, wherein said multiwell system is produced by extrusion.

The invention further provides a method for producing a multiwell system according to the invention, comprising steps of
melting said biocompatible material in a thermal jacket;
extruding the melted, biocompatible, material under pressure through a nozzle to form a plotted fiber;
said extrusion step is repeated, thereby depositing a subsequent plotted fiber in parallel at a distance of between 0.125 and 2.5 mm next to the last deposited fiber until a layer is formed.

The method can suitably be carried out using a 3D plotter, preferably wherein said 3D plotter is controlled by CAD software. The step of controlling the 3D plotter preferably comprises steps of providing a design data file of coordinates representing a three-dimensional design of the multiwell system according to the invention and generating control signals based on said design data file dispensing a strand of a biocompatible material in a fluent state in response to said control signals and treating said strand of biocompatible material after dispensing in a controlled time and dimensional relationship to said dispensing of said biocompatible material so that said material undergoes a transition to a fixed physical state in which said biocompatible material is solidified in an accurate form of said multiwell system.

Preferably, said 3D plotter is a Bioplotter device (Envisiontec GmbH, Germany) or a Bioscaffolder (SysEng GmbH, Germany). Preferably said pressure is between 0.4 Bar and 4 Bar. Pressure may be varied depending on the biocompatible material deposited. Preferably, nitrogen gas is used to create pressure. Preferably, the starting fiber deposition speed is at least 320 mm/min and may be up to 1800 mm/min depending on the composition of the biocompatible material. In order to create a closed bottom, preferably the first layer deposited is a closed layer. Alternatively, a closed layer may also be achieved by choosing the dimensions of a subsequently deposited layer such that openings in the first layer are closed by material of a subsequent layer.

A subsequent layer is deposited on the previous layer, wherein the fibers forming said subsequent layer are deposited at an angle relative to the fibers of the previous layer; repeating said step wherein said subsequent layer is deposited until the desired height is achieved. In principle, any angle may be used, but preferably said angle is between 1 and 90 degrees, more preferably an angle between 10 and 90 degrees and even more preferably between 45 and 90 degrees is used. Most preferably, an angle of approximately 90 degrees is used. Of course, said angle may be varied within one embodiment of the multiwall system and/or between layers.

Said layer is made of a multitude of plotted fibers in parallel to each other in the same horizontal plane (in the Z axis). A layer may consist of a multitude of separate plotted fibers or may consist of a single connected plotted fiber as is shown in FIG. 2A (e) and the top figure of FIG. 2B. Different types of plotted fibers may be used, as can be regulated by varying the opening size and/or form of the nozzle. A single round hole produces a round fiber. Alternatively, a double nozzle may be used which creates a fiber which is higher than it is thick, which is an easy way to create height in fewer layers. The extrusion of fibers is done layer-by-layer at defined distances of between 0.125 and 2.0 mm as preferably set in CAD software. This means that as layers are deposited on top of each other (in the Z axis), closed wells can be made by depositing fibers on top of each other at a controlled temperature, preferably between 25 and 250° C., at a pressure between 0.1 and 6 bar, and using a deposition speed between 40 and 2400 mm/min. These parameters are important to control to determine whether the wells will be opened or closed. The well dimensions can be defined by increasing or decreasing fiber distances in the XY axis. Height of the multiwell system is created by depositing a subsequent layer on top of the previous layer, whereby the fibers forming said subsequent layer are deposited at an angle preferably between 1 and 90 degrees relative to the fibers of the previous layer. When an angle of approximately 90 degrees is use, rectangular wells are created. Fibers can be extruded at different angles, thus making well channels with different architectures.

Methods for Preparing 3D Tissue Constructs

The invention provides a method for preparing a 3D tissue construct from cells, comprising steps of introducing medium comprising a number of cells in a multiwell system according to the invention and culturing the introduced cells to allow the cells to form a 3D tissue construct. Some cell types need to be present in a sufficient number in order to achieve a 3D tissue construct. A skilled person can easily determine whether a minimum number is required by making dilution series. Preferably, said cells are of a cell type which under in-vivo conditions can form a 3D tissue. Virtually any kind of cell can be used. Cells which require attachment to a surface in order to survive are preferred. Preferred cells include stem cells from all sources including mesenchymal, embryonic stem cells, but preferably not human embryonic stem cells which are obtained by a method which involves the destruction of human embryos. Other preferred cells comprise cells from different vertebrates, preferably mammals, more preferably from humans, mice, rabbits, goats or cows. In certain embodiments, preferred cells are from different tissues, and include cardiomyocytes, neurons, brain cells, osteocytes, chondrocytes, adipocytes, fibroblasts, keratinocytes, smooth muscle cells, endothelial cells, osteoblasts, lymphocytes, macrophages, T-cells, or tumor cells. In a preferred embodiment, said microwell system is used for studying the effects of pharmaceutical compounds on the formation of 3D tissue constructs. Preferably, said system is also used to study the effects of potential anti-tumor compounds on tumor-tissue development. Preferably, said first type of cells comprises stem cells, preferably human Mesenchymal Stem Cells (hMSC) or chondrocytes, preferably primary chondrocytes, more preferably bovine primary chondrocytes. Preferably, said hMSCs are obtained from an acetabulum of a human donor. Preferably, said hMSCs are essentially free of non-adherent cells. Preferably, said hMSC are cultured in-vitro, preferably for at least 4 days, before said step of introducing them into said well.

Preferably said chondrocytes originate from articular cartilage. The number of said first type of cells which is sufficient to allow the formation of a 3D tissue construct depends on the cell type which is used. The inventors have found that a too low number of cells seeded will not form a 3D tissue construct, no matter how long cells are cultured. A skilled person will have no difficulty in finding out what number is sufficient, for example by making a dilution series and determine whether a 3D tissue construct is formed within approximately a month. The inventors have also observed a strong correlation between tissue area and the number of cells. Therefore, the number of cells seeded per well in said method is preferably at least 4000, but more preferably higher, i.e. 5000, 6000, 7000, 8000, 9000, 10000, 15000, 20000 or 25000 cells. In a preferred embodiment, said method comprises a step of coculturing the cells, which are of a first type of cells, preferably hMSCs, with cells of a second cell type, which stimulate the growth of the cells of the first cell type. chondrocytes. When a coculture is used, the ratio between cells of the first type: cells of the second type (preferably Chondrocytes:hMSCs) is between 0.1:0.9 and 0.9:0.1. An advantage is that coculturing further stimulates the 3D tissue construct formation. Preferably, the maximum number of totals cells in a well is $2.5 \times 10^4$. Preferably, the cells or 3D tissue constructs of at least 2 wells are exposed to a different culturing condition, including a different number of cells which are seeded. In principle, any compound or culture conditions which potentially has an effect on a relevant parameter of a cell of said 3D tissue construct may be tested.

In a preferred embodiment, 3D tissue constructs are formed in 2 or more wells of the multiwell system and wherein different culturing conditions are applied to the 2 or more wells. Preferably, said 2 or more wells means at least 3, 4, 5, 6, 7, 8, 9, 10, 15, 20, 25, 30 wells. Determining an effect of said compound or said culturing condition may be done by techniques well known in the art and include but is not limited to determination of the histology, quantification of cells and/or morphology of the cells or 3D tissue constructs present in the wells which were exposed to said compound or said culture condition. Suitable technologies include different types of microscopy and staining techniques. In a preferred embodiment, said method is performed using automatic microscopy analysis, preferably using multiple fluorescent labels. Preferably said effect is determined using a method that avoid histological processing [as described in Bratlie, K. M., et al., Plos One, 2010. 5(3): p. 1-8, Judex, S., et al., Methods, 2010. 50(1): p. 14-19, and Bhargava, R., et al., Biochimica Et Biophysica Acta-Biomembranes, 2006. 1758 (7): p. 830-845] and improve the quantification and sensitivity of said method for preparing a 3D tissue construct according to the invention, preferably when performed in vivo. For example, in vivo imaging of cathepsin activity and macrophages or other enzymes could be adapted to the multiwell system. This method is fully described in Bratlie, K. M., et al., Plos One, 2010. 5(3): p. 1-8.

Another advantage of the multiwell systems according to the invention is that they can be made small enough to fit inside a transplantation pocket of an animal. Because of their size, these multiwell systems can be implanted in an animal without causing much suffering. This is a great advantage, as implanting a multiwell system in an animal means that the formation of 3D tissue constructs can be done without having to refresh medium, as the supply of nutrients by the animal has proven to be sufficient. Due to the small volumes, the g force on the volume of cells and medium comprising for example reagents to be tested is so small that there is no risk of cross contaminating the contents of different wells by the contents of other wells.

Therefore, in a preferred embodiment, said step of culturing cells in a well of said multiwell system according to the invention is performed in a pocket of a suitable animal. Preferably, said animal is a vertebrate, more preferably a mammal. Most preferred animals comprise rats, mice, preferably nude mice, goats and rabbits. Preferably, said animal is a non-human animal. However, it may also be advantageous to use the multiwell system as a screening device in humans.

Preferably a pocket is chosen where a transplant causes minimal harm or inconvenience to said animal. Pocket sites which are suitable to transplant a multiwell system into vary between animals. A skilled person will have no difficulty in identifying suitable pockets. In mice, preferred pockets are in the posterior-lateral side of the back.

Animal testing and laboratory expenses are inversely proportional to the number of wells implanted per pocket. Therefore, the invention further provides an animal comprising a multiwell system according to the invention, wherein said multiwell system comprises cells.

The invention is now illustrated by a number of examples which are not limiting the scope of the invention.

EXAMPLES

Materials and Methods

Well Macroarray Fabrication

A Bioplotter device (Envisiontec GmbH, Germany), which is a XYZ plotter, was used to make the well macroarrays. 3D cubical models were CAD-designed with Rhinoceros software (Delft, The Netherlands) and loaded on the Bioplotter CAM software (PrimCAM, Einsiedeln, Switzerland). In addition, materials were loaded in a steel syringe for thermoplastic polymers or plastic syringe for hydrogels. Then, the syringe-cartridge unit was mounted on the mobile X-arm of the apparatus. A nitrogen variable pressure between 0.4 Bar and 4 Bar was applied to the syringe for material extrusion. Pressure varied depending on the biocompatible material deposited. The combination of software and physical set-up resulted in the extrusion of materials in the form of fibers deposited layer-by-layer onto a stage. The starting fiber deposition speed varied from 320 mm/min and 1800 mm/min depending on the biocompatible material composition.

To obtain macroarrays in a matrix form (columns×rows), closed wells were made by depositing fibers on top of each other at a 90° angle to obtain rectangular wells (FIG. 1). The well XY dimensions were defined by increasing or decreasing fiber distances in the XY axis. In addition, the well height was defined by the height of the cubical model (FIG. 1C-E), where the first layer deposited was closed or not depending on the design. Macro-wells were made with four materials with their respective parameters as shown on Table 1.

TABLE 1

Materials used to make macro-arrays and processing parameters.

| Material | Cartridge Temperature [° C.] | 1st layer Strand Distance [mm] | 2nd layer and higher strand distance [mm] | Layer thickness [mm] | Inner Needle diameter [mm] |
|---|---|---|---|---|---|
| PEOT/PBT 300/55/45 | 200 | 0.3 | 1.5 | 0.2 | 0.4 |
| PEOT/PBT 1000/70/30 | 190 | 0.3 | 1.5 | 0.2 | 0.25 |
| Polylactic acid | 220 | 0.3 | 1.5 | 0.2 | 0.4 |
| Alginate | 25 | 0.5 | 3 | 0.2 | 0.5 |

Furthermore, different architecture designs were fabricated to maximize the number of macroarray wells and to create co-culture macroarray systems as shown on FIGS. 9E-F. For these macroarrays of 4 mm in height, the same processing parameters as shown on table 1 were implemented depending on the material. For design on FIG. 9E, a third layer strand distance (0.5 mm) in the middle of the well macroarray height (at 2 mm) was introduced. Alternatively, this middle layer can be created by combining rapid prototyping with spinning technologies, e.g. electrospinning (FIG. 9G). For these designs, first and second layer strand distances were maintained elsewhere as shown on table 1. Furthermore, the design on FIG. 9F involved first depositing second layer strand distances (Table 1) to maintain an opened bottom. Then, depositing the first layer strand distance (Table 1) in the middle of the well macroarray height (at 2 mm). Subsequently, layer deposition with second layer strand distances (Table 1) was resumed.

Two-Dimensional PEOT/PBT Discs 2D substrates of 300PEOT55PBT45 were fabricated by a hot-embossed compression molding technique. Two silicon wafers served as support and defined the molded surface. A stainless steel mold with circular features through holes of 2.2 cm in diameter was placed in between the molds. Granules of 300PEOT55PBT45 were placed inside the mold to fill up the mold cavities upon polymer melting.

Silicon supports were cleaned by immersion in piranha solution (3:1 concentrated $H_2SO_4$/33% aqueous $H_2O_2$) for 15 min. These were rinsed with water and dried in $N_2$. Then, they were functionalized with 1H,1H,2H,2H-perfluorodecyl-trichlorosilane (ABCR). After, these were deposited in gas phase that served as anti-adhesion layer to ease the polymer-support separation. For the hot embossing processing, a hydraulic press equipped with a water cooling system and temperature control (Fontune Holland, the Netherlands) was used. The 300PEOT55PBT45 was placed on top of the silicon support and in the aperture of the mold. Then, the system was heated up to a temperature of 180° C. and 10 bars were applied. After 5 minutes the system cooled down to 60° C. and the pressure was released. The mold and the supports were manually separated and the 2D disc released from the mold.

hMSCs Culture hMSCs were isolated, cultured and cryopreserved as described by Both, S. K. et al., Tissue Engineering, 2007. 13(1): p. 3-9. hMSCs were obtained from the acetabulum of three donors who were undergoing total hip replacement surgery and gave informed consent for bone marrow biopsy, approved by the local medical ethical committee. Gender and donor age were: Donor 1: Female, 81 years. Donor 2: Male, 65 years. Donor 3: Female, 66 years. Mono-nucleated cells were counted in the aspirate and plated at a density of 500,000 cells/cm$^2$ on tissue culture plastic (Nunc, Thermo Fischer Scientific, Roskilde, Denmark).

Cells were cultured for four to five days in α-minimal essential medium (αMEM) proliferation medium in an incubator with a humidified atmosphere of 5% carbon dioxide at 37° C. The αMEM proliferation medium contained minimal essential medium (GIBCO, Carlsbad, Calif.); 10% fetal bovine serum of a selected batch (FBS; Biowhittaker, lot: 8SB0002; Loza, Verviers, Belgium); 0.2 mM 1-ascorbic-acid-2-phosphate (Sigma, St. Louis, Mo.); penicillin G (100 Units/ml, Invitrogen, Carlsbad, Calif.); streptomycin (100 μg/ml, Invitrogen); 2 mM 1-glutamine (Sigma) and 1 ng/ml basic fibroblast growth factor (Instruchemie, Delfzijl, The Netherlands).

After the four to five day culture period, non-adherent cells and αMEM proliferation medium were discarded. Adherent cells were thoroughly washed twice with PBS phosphate-buffered-saline (PBS, Sigma) and αMEM proliferation medium was refreshed. Adherent cells were proliferated for two passages and cryopreserved. For well macroarray culture, cryopreserved hMSCs—passage 2—were recounted and plated at 1,000 cells/cm2 on tissue culture plastic (Nunc) in αMEM proliferation media. hMSCs were expanded for one week with one refreshment of αMEM proliferation media.

Chondrocyte Culture

Primary chondrocytes were isolated through collagenase digestion from articular cartilage harvested from an 18-month old bovine knee joint. Cells were aggregated with 300 μg/ml of fibronectin (Invitrogen). Primary chondrocytes were expanded for one passage with medium refreshments twice a week. The chondrocyte culture medium contained HEPES (Invitrogen)-buffered DMEM (Invitrogen) supplemented with 10% fetal bovine serum (FBS; Biowhittaker, lot: 8SB0002; Loza, Verviers, Belgium), 100 μg/ml streptomycin (Invitrogen), 0.1 mM nonessential amino acids (Sigma-Aldrich), 0.2 mM ascorbic acid 2-phosphate (Invitrogen), 0.4 mM proline (Sigma-Aldrich) and 100 units/ml penicillin (Invitrogen).

Macroarray Sterilization and Conditioning for Cell Culture

Macroarrays were sterilized with 70% Ethanol solution for 15 min. After, macroarrays were washed and incubated at room temperature for two hours with sterile PBS. We repeated this washing step three times. Then, macroarrays were incubated in αMEM proliferation media overnight at 37° C. before seeding.

Well Macroarray Seeding

From a cell suspension of $5 \times 10^6$ cells/ml, hMSCs and chondrocytes were centrifuged at 200 Relative Centrifugal Force (RCF) and re-suspended in 0.2 ml of medium. From this cell suspension, dilutions and the coculture were prepared with a maximum of $2.5 \times 10^4$ cells in 1 μl volume seeded per well. Every subcondition (i.e. cell dilutions and coculture ratios), was seeded in all the wells of a column. For example, in a 3×3 macroarray, three replicates or three wells were seeded with the same sub-condition. Seeded well macroarrays were incubated for 20 min at 37° C. in a humid atmosphere with 5% $CO^2$. Non-detached cells in a macroarray were removed by washing with culture medium, then these were placed in a well of a 25-well plate (Nunc), and covered with the culture medium of the seeded cell type and incubated at 37° C.

Coculture hMSCs:Chondrocytes were seeded in well macroarrays in αMEM proliferation media. Three different mixes of hMSCs and Chondrocytes, with hMSCs:chondrocytes ratios of 0:1, 0.5:0.5 and 1:0 were seeded in triplicates of three wells of a 3×3 macroarray. $2.5 \times 10^4$ were the maximum number of cells seeded in a well with ratios obtained prior to well macroarray seeding.

Chondrogenic Differentiation

Macroarrays with hMSCs dilutions were cultured for 4 weeks in chondrogenic differentiation medium. Chondrogenic differentiation medium was composed of DMEM (GIBCO) with the following supplements: 0.01 μg/ml TGFβ1 (RnD Systems, UK), 0.1 nM Dex, 100 μg/ml sodium pyruvate (Sigma), 40 μg/ml L-proline (Sigma), 100 μg/ml streptomycin, 1× insulin-transferrin-selenite (ITS+ (Sigma), and 100 U/ml of penicillin. Medium refreshment occurred twice a week.

Immunohistochemistry

Click-iT® EdU Alexa Fluor® 488 Imaging Kit (Invitrogen) was used to image the DNA synthesis by proliferating hMSCs in well macroarrays. Wells with hMSCs were incubated in a 1:1 solution of EDU in proliferation medium at 37° C. for 24 h. Then, these were fixed in 1% formalin (Sigma-Aldrich) for 30 min. 3D scaffolds were embedded in Tissue-Tek OCT (Qiagen, The Netherlands) and placed at −80° C. overnight. 5 μm sections were then cut in a cryomicrotome. After, sections on a slide were permeabilized and washed with the secondary antibody (horseradish peroxidase conjugated goat-anti-human immunoglobulin antibody, Dako, Denmark) and counterstained with DAPI (Invitrogen). Fluorescent microscopy was used to visualize EdU (DNA) and DAPI (cell nuclei) signals.

Implantation in Nude Mice

Nude mice studies were performed after consent from the ethical committee for animal studies (DEC-GDL Utrecht, The Netherlands). Six-week-old nude mice (Hdcpb:NMRI-nu Harlan, The Netherlands) were anaesthetized with 0.02 ml of a 3.5:3:1 mixture of ketamine (100 μg/ml): Xylazine (20 μg/ml): atropine (0.5 μg/ml). Four 3×3 macroarray wells containing each of the conditions and sub-conditions were subcutaneously implanted per mouse in the posterior-lateral side of the back and sutured. The four conditions implanted were: hMSCs, differentiated hMSCs, chondrocytes, and hMSCs: chondrocytes coculture. The 3 sub-conditions tested for each condition within each macroarray are referenced on Table 2. After 2 weeks (n=10) and 4 weeks (n=10) mice were euthanized via $CO_2$ asphyxiation and macroarrays were excised and processed for analysis.

TABLE 2

Subconditions screened in the well macroarrays subcutaneously implanted in nude mice.

| Number | Sub-condition |
| --- | --- |
| 1 | hMSCs 4X, wk 2 |
| 2 | hMSCs 2X, wk 2 |
| 3 | hMSCs 1X, wk 2 |
| 4 | hMSCs 4X, wk 4 |
| 5 | hMSCs 2X, wk 4 |
| 6 | hMSCs 1X, wk 4 |
| 7 | Diff. hMSCs 4X, wk 2 |
| 8 | Diff. hMSCs 2X, wk 2 |
| 9 | Diff. hMSCs 1X, wk 2 |
| 10 | Diff. hMSCs 4X, wk 4 |
| 11 | Diff. hMSCs 2X, wk 4 |
| 12 | Diff. hMSCs 1X, wk 4 |
| 13 | BPCs 4X, wk 2 |
| 14 | BPCs 2X, wk 2 |
| 15 | BPCs 1X, wk 2 |
| 16 | BPCs 4X, wk 4 |
| 17 | BPCs 2X, wk 4 |
| 18 | BPCs 1X, wk 4 |
| 19 | hMSCs:BPCs 0:1, wk 2 |
| 20 | hMSCs:BPCs 0.5:0.5, wk 2 |
| 21 | hMSCs:BPCs 0:1, wk 4 |
| 22 | hMSCs:BPCs, 0.5:0.5, wk 4 |
| 23 | hMSCs:BPCs, 1:0, wk 4 |
| 24* | hMSCs:BPCs, 1:0, wk 2 |

*Quantification was not possible.

Histology

3×3 macroarray wells implanted in nude mice were washed in PBS and fixed in 10% Formalin at 4° C. overnight. After washing in PBS, macroarrays were cut into rows with a sharp blade and stained with 1% Methylene blue. For hematoxylin/eosin (H&E) staining, after cutting a macrorray row (3 wells) with a sharp blade, samples were dehydrated and embedded in Glycol Methyl Acrylate (GMA). 5 μm sections were cut with a microtome and stained with H&E.

Tissue Quantification

A row in the 3×3 macroarray matrix stained with 1% methylene blue was imaged with a stereomicroscope. Images were processed by cutting the images of wells in a row and converting them to a binary pixel image (FIG. 10E) with ImageJ software (Free source). Black and white pixels within an image of a well were quantified with the histogram function in ImageJ, where the total pixels and tissue pixels were obtained. The tissue/total pixels ratio was obtained for each well in a row of a 3×3 macroarray implanted.

Statistical Analysis

Statistical significance was set at $p < 0.05$. 3×3 Macroarray wells were implanted in nude mice (n=20) for explantation on weeks 2 and 4. Linear regression was performed for the means of tissue/total ratio [pixel/pixel] vs. cell number for each sub-condition (Table 2) for n=10 mice per time point. Anova analysis between and within means of tissue/total ratio [pixel/pixel] of all sub-conditions was performed with the anova1 and multcompare functions of Matlab (version 7.0.4 release 2007a; Mathworks, Natick, Mass.) on a windows-based system.

Results

Free-form fabrication was used to develop the HTS system. This allowed us to define both the well architecture and the number of wells in column×rows arrays (FIG. 2). Rectangular 90°-angle wells were seeded with hMSCs and cultured in time. In this manner, it was observed that there was an inverse correlation between hMSCs organization and well size (FIG. 3): As the well size increased (FIG. 3A-C), hMSCs organized from 3D aggregates to mono-layers, thus showing that hMSCs organization could be controlled through the well volume and culture time.

In addition, different cell dilutions seeded into different wells illustrated that it was possible to maintain different levels of hMSCs organization in different wells (FIG. 5) in the same macroarray. The well with the highest number of hMSCs contained 3D aggregates whereas hMSCs dilutions produced wells with monolayer hMSCs cultures. This showed that different conditions could be maintained in different wells in an array style. On the contrary, hMSCs on 2D PEOT PBT discs did not form 3D aggregates neither in time nor as a function of cell numbers (FIG. 4).

The time-dependent nature of hMSCs proliferation was exploited to produce hMSCs aggregates of different sizes (FIG. 6) in different wells of the same macroarray. As the culture time increased, hMSCs proliferated and formed larger aggregates (FIG. 6).

Well macrorrays were tested in vivo in 3×3 well macroarrays custom-made to fit in a mouse pocket. Each of the 9 wells within the implanted 3×3 macroarray measured 1 mm×1 mm×1.8 mm. (FIG. 3B). hMSCs, differentiated hMSCs, primary bovine chondrocytes (PBCs) and a hMSCs:PBCs co-culture, for a total of four conditions were evaluated in each of four mouse pockets (FIG. 10). For each condition, 1×, 2× and 4× cell dilutions (FIG. 10) were made for a total of three sub-conditions. Each sub-condition was seeded into each well column to obtain three replicates in each 3×3 well macroarray.

Explantations occurred on weeks 2 and 4, with 10 mice sacrificed on each week to evaluate the conditions and sub-conditions implanted in each macroarray. FIG. 10 shows tissue (host and implanted) penetration in all sub-conditions. Tissue bulges were present in all wells. Consequently, tissue coverage was quantified. This was done by quantifying the tissue (host and implanted) coverage ratio of tissue pixels over total area pixels (FIG. 10E).

Linear regression analysis was performed on the means of tissue area vs. cell numbers for the three cell types implanted in macroarrays (FIG. 11). This analysis showed that there was strong linear correlation for tissue area vs. cell numbers for hMSCs week 2 ($R^2$=0.84, FIG. 11A) and for primary chondrocytes week 4 ($R^2$=0.94, FIG. 11C). All other subconditions did not show a strong correlation coefficient.

To compare subconditions between each other, ANOVA and multiple comparison analysis of the means were performed (FIG. 12, numbers of subconditions on table 2, ANOVA table on table 3). The box plots (FIG. 12A) of each subcondition showed that there were different subconditions from each other (p=0.0058 on Table 3). But, multiple comparison analysis of each of the means showed that these differences were not significant (FIG. 12B). The ratio of tissue coverage was not significantly different between conditions in any macroarray.

TABLE 3

ANOVA table comparing means of all sub-conditions

| | Source | | | | |
|---|---|---|---|---|---|
| | SS | df | MS | F | Prob > F |
| Sub-conditions | 0.53 | 22 | 0.024 | 2.42 | 0.0058 |
| Error | 0.46 | 46 | 0.011 | | |
| Total | 0.99 | 68 | | | |

Representative histological sections of the host tissue above were stained with H&E (FIG. 13). Host tissue above the wells of the hMSCs (FIG. 13A) condition showed lumens of larger size and in higher numbers than on the other three conditions (FIG. 13B-D).

Screening in Vitro

To demonstrate that conditions seeded in 3D HTS system can be quantified with laboratory equipment, 3D HTS systems were designed with over 200 wells that fit an automatic confocal microscope (FIG. 14). The 3D HTS systems were of two types; one made of polylactic acid (PLLA) and manufactured via fused deposition modeling (FIG. 14A), and the other made of an acrylic photopolymerizable resin and manufactured via stereolithography (FIG. 14F-G). To show that inert and biological compounds can be screened in a high throughput manner in the 3D HTS system, we seeded dyes (FIG. 14B-C, H-I), beads (FIG. 14D) and fluorescent markers (FIG. 14J) in the 3D HTS systems. As depicted in FIGS. 14B-C and H-I, dyes of different colors (red, blue, yellow, purple, and white) were seeded and could be observed with stereomicroscopy on both PLLA and resin 3D HTS systems. To quantify the intensity of light emitted from each well, fluorescent beads were seeded at three dilutions in wells made of PLLA (FIG. 14D). The mean fluorescent intensity (n=3), measured in an automatic confocal microscope, showed that the light intensity significantly decreased with increasing dilution factor (FIG. 14E). When fluorescent markers rhodamine and FITC were seeded at different dilutions in resin-made wells (FIG. 14J), these also showed a correlation between dilution factor and mean light intensity (FIG. 14K). These results further show that 3D HTS systems can be adapted to laboratory equipment and implemented in the screening and quantification of molecules.

Screening in Vivo

The 3D HTS system can be used to screen conditions and compounds that can lead to positive hits for a specific application. To further test this concept in animals, a study was performed screening cell types or conditions that have been shown to induce tissue regeneration in vivo (Gurkan U A, Akkus O. The mechanical environment of bone marrow: a review. Ann Biomed Eng. 36:1978-91. 2000). In the study, two cell types; human mesenchymal stem cells (hMSCs) and bovine primary chondrocytes; a co-culture of them; and empty 3D HTS systems comprised the 4 conditions tested in wells made of PEOT/PBT. 9 wells of a 3D HTS system of size 3×3 were seeded with 3 sub-conditions and implanted subcutaneously in a pocket of a nude mouse. For the hMSCs and chondrocytes, the three sub-conditions consisted of three dilutions: 1×, 2× and 4× with a maximum of 25,000 cells in a well. For the co-culture, the three sub-conditions consisted of three hMSCs:Chondrocyte ratios: 80:20, 50:50 and 20:80 also with a maximum of 25,000 cells seeded in a well. Each sub-condition was seeded in three wells of the same macroarray, thus for each macroarray, the sample number per sub-condition was n=3. The empty 3D HTS system acted as the control for tissue regeneration without cells. Four 3D HTS systems were implanted per mouse in a total of 20 nude mice, each containing the 4 described conditions and their respective sub-conditions. 3D HTS systems were explanted from 10 mice after 2 weeks, and the other 10 mice after 4 weeks to assess the tissue in of the wells.

For all conditions, explanted 3D HTS systems were embedded in paraffin and sectioned every 5 μm with a microtome. After, sections were placed on glass slides and stained with haematoxylin and counterstained with eosin (FIG. 15). Because different sub-conditions, showed potential differences in the amount of tissue in a well, the tissue percent area was quantified in all conditions to determine positive hits for tissue regeneration inside a well. Image analysis was performed in the area containing each well on the slides (FIG. 15) and subsequently the percent area of tissue was obtained from the total area in the rectangle for at least 3 representative sections for each well.

To visualize the trends observed in the sections of the implanted 3D HTS systems, the percent area of tissue for each sub-condition was plotted at 2 and 4 weeks after implantation (FIG. 16). The percent area of tissue in a well varied depending on the cell type and sub-condition tested. For example, in wells containing hMSCs (FIG. 16A) the percent area of tissue increased with lower dilutions and when compared to the control. This trend was not necessarily present in wells seeded with chondrocytes (FIG. 16B), where week 2 and week 4 mice showed conflicting trends. Despite seeding the same total amount of cells in all wells, the wells seeded with the co-culture also showed lower tissue percent areas for wells containing the lower amounts of chondrocytes (FIG. 16C).

To determine whether there were any significant trends in tissue percent area, we obtained the mean of the percent area of tissue (n=3) for all sub-conditions in all 20 mice. Then, ANOVA analysis of the means was performed for each 3D HTS system, where sub-conditions and control were compared between each other for each statistically independent mouse. The result of these analyses was that some mice showed significant (p<0.05) differences in the percent area of tissue, whereas others did not (Tables 4, 5 and 6). For example, 50% of the mice showed a significant difference in the percent area of tissue between the 1× dilution and the control on week 4. This means that for half of the mice on week 4, the higher the cell number (1× dilution), the higher the tissue percent area in a well. For some sub-conditions of chondrocytes, half the mice showed a significantly higher percent area of tissue in some sub-conditions (Table 5). Since the co-cultures shared the same total amount of cells (25,000), it was interesting that 56% of the mice showed significantly higher percent area of tissue when the higher number of hMSCs was seeded (80:20) (Table 6).

For tissue regeneration, these results suggest that hMSCs positively induce higher amounts of tissue when compared to chondrocytes and controls. To understand the biological nature of tissue in wells containing hMSCs, we stained slides with tissue markers specific for collagen and proteoglycan formation (FIGS. 17 and 18).

TABLE 4

The differences in tissue percent area for hMSCs dilutions were significant in some animals. The table shows the number of animals (%) showing a significant difference (p < 0.05) in the tissue percent area after ANOVA analysis of means. The tissue percent area for three dilutions and control were compared with each other.

|  | 1X | 2X | 4X | Control |
|---|---|---|---|---|
| 1X |  | *0%* | 33% | 25% |
| 2X | 13% |  | *11%* | 25% |
| 4X | 0% | 13% |  | *50%* |
| Control | 50% | 50% | 38% |  |

Italics and bolded text show the number of animals showing statistically significant differences on week 2 and 4, respectively.

TABLE 5

The differences in tissue percent area for chondrocytes dilutions were significant in some animals. The table shows the number of animals (%) showing a significant difference (p < 0.05) in the tissue percent area after ANOVA analysis of means. The tissue percent area for three dilutions and control were compared with each other.

|  | 1X | 2X | 4X | Control |
|---|---|---|---|---|
| 1X |  | *25%* | 25% | 38% |
| 2X | 50% |  | *50%* | 50% |
| 4X | 25% | 0% |  | 38% |
| Control | 25% | 25% | 25% |  |

Italics and bolded text show the number of animals showing statistically significant differences on week 2 and 4, respectively.

TABLE 6

The differences in tissue percent area for the co-culture ratios were significant in some animals. The table shows the number of animals (%) showing a significant difference (p < 0.05) in the tissue percent area after ANOVA analysis of means. The tissue percent area for three hMSCs:Chondrocytes ratios and control were compared with each other.

| hmscs:chondrocytes | 80/20 | 50/50 | 20/80 | Control |
|---|---|---|---|---|
| 80/20 |  | *11%* | 22% | 44% |
| 50/50 | 33% |  | *33%* | 44% |
| 20/80 | 33% | 11% |  | *11%* |
| Control | 56% | 11% | 33% |  |

Italics and bolded text show the number of animals showing statistically significant differences on week 2 and 4, respectively.

To identify positive hits for tissue regeneration, we investigated the tissue organization inside of the wells by staining for collagen and muscle tissue (FIG. 17). Control 3D HTS systems showed muscle tissue contained within the wells (FIG. 17A) whereas wells containing hMSCs dilutions showed no muscle tissue (FIG. 17B-C). Furthermore, 1× and 2× hMSCs dilutions showed aligned collagen fibers and blood vessels, which showed that wells containing over 12,500 hMSCs (2× dilution) positively support a higher degree of tissue organization and regeneration.

To identify the type of tissue contained within the wells, glucosaminoglycans were stained as a marker of cartilage tissue (FIG. 18). When compared to controls, the co-culture containing higher amounts of hMSCs (80:20) was positive for glucosaminoglycans (FIG. 18D). From percent tissue area, collagen and glucosaminoglycans markers, we concluded that the wells that positively yield tissue regeneration were those containing hMSCs above 12,500 cells (1× and 2× dilution) and hMSCs:Chondrocyte ratios equal to 80:20. Thus, these three sub-conditions are positive hits, which are an example on how 3D HTS systems can be implemented in the in vivo screening of cells and compounds for therapeutics, drug discovery and preclinical research.

Conclusions

In vivo HTS reduces the number of animals used in animal experiments. Thousands of wells can be made with a wide range of materials, where the HTS size can be defined for the implantation site of the tested animal. This significantly reduces financial costs and lives of vertebrate animals used in the chemical, biotechnological, pharmaceutical, and biomedical industries among others.

The invention claimed is:

1. A method for preparing a 3D tissue construct from cells comprising the steps of:
 a) introducing a medium comprising cells in a well of a multiwell system,
  wherein the multiwell system comprises at least 3 wells, the wells comprises sidewalls made of alginate, polylactic acid or PEOT/PBT, wherein said wells have a volume between 0.125 and 4.0 mm$^3$, a wall thickness of at least 50 microns and a closed bottom, wherein the multiwell system does not comprise a 3D synthetic polymer scaffold and the initial number of cells per well is between 4,000 and 25,000; and
 b) culturing the cells to obtain a 3D tissue construct.

2. The method according to claim 1, wherein the wells have an inner diameter larger than 0.5 mm.

3. The method according to claim 1, wherein the cells are stem cells, preferably human Mesenchymal Stem Cells (hMSC), or chondrocytes.

4. The method according to claim 1, wherein the cells are of a first type of cells and wherein cells of a second type are introduced in the well and cocultured with the cells of the first cell type in step b, wherein the cells of the second type stimulate the growth of cells of the first type in the formation of said 3D tissue construct.

5. The method according to claim 1, wherein 3D tissue constructs are formed in 2 or more wells of the multiwell system and wherein different culturing conditions are applied to the 2 or more wells.

6. The method according to claim 5, wherein the multiwell system is implanted in a pocket of a suitable animal.

7. A method for producing a multiwell system for use for preparing a 3D tissue construct from cells, comprising steps of:
 a) melting alginate, polylactic acid, or PEOT/PBT in a thermal jacket;
 b) extruding the melted alginate, polylactic acid, or PEOT/PBT under pressure through a nozzle to form a plotted fiber;
 c) repeating step b), thereby depositing a subsequent plotted fiber in parallel at a distance of between 0.125 and 2.0 mm next to the last deposited fiber until a layer of alginate, polylactic acid, or PEOT/PBT is formed;
 d) depositing a subsequent layer on the previous layer, wherein the fibers forming said subsequent layer are deposited at an angle preferably between 10 and 90 degrees relative to the fibers of the previous layer; and
 e) repeating step d) until a desired height is achieved;
 wherein the method produces a multiwell system comprising at least 3 wells, the wells comprise sidewalls made of alginate, polylactic acid or PEOT/PBT, wherein said wells have a volume between 0.125 and 4.0 mm$^3$, a wall thickness of at least 50 microns and a closed bottom, and wherein the multiwell system does not comprise a 3D synthetic polymer scaffold.

8. A multiwell system comprising at least 3 wells, wherein the wells comprise sidewalls made of alginate, polylactic acid or PEOT/PBT, wherein said wells have a volume between 0.125 and 4.0 mm$^3$, a wall thickness of at least 50 microns and a closed bottom, and wherein the multiwell system does not comprise a 3D synthetic polymer scaffold.

9. The multiwell system according to claim 8, wherein said alginate, polylactic acid or PEOT/PBT has been approved for use in an animal by a legal authority.

* * * * *